United States Patent
Motegi

(10) Patent No.: US 10,285,635 B2
(45) Date of Patent: May 14, 2019

(54) PERIODONTAL INDEX CREATION METHOD, PERIODONTAL INDEX CREATION APPARATUS, PERIODONTAL INDEX CREATION PROGRAM, AND RECORDING MEDIUM HAVING RECORDS OF PERIODONTAL INDEX CREATION PROGRAM, AND PERIODONTITIS DIAGNOSIS METHOD, PERIODONTITIS DIAGNOSIS APPARATUS, PERIODONTITIS DIAGNOSIS PROGRAM, AND RECORDING MEDIUM HAVING RECORDS OF PERIODONTITIS DIAGNOSIS PROGRAM

(71) Applicant: Yoshio Motegi, Fuefuki (JP)

(72) Inventor: Yoshio Motegi, Fuefuki (JP)

( * ) Notice: Subject to any disclaimer, the term of this patent is extended or adjusted under 35 U.S.C. 154(b) by 72 days.

(21) Appl. No.: 14/389,199

(22) PCT Filed: Jul. 31, 2013

(86) PCT No.: PCT/JP2013/070773
§ 371 (c)(1),
(2) Date: Sep. 29, 2014

(87) PCT Pub. No.: WO2015/015602
PCT Pub. Date: Feb. 5, 2015

(65) Prior Publication Data
US 2016/0206238 A1    Jul. 21, 2016

(51) Int. Cl.
*A61B 5/00*    (2006.01)
*A61B 10/00*    (2006.01)
(Continued)

(52) U.S. Cl.
CPC ............ *A61B 5/4542* (2013.01); *A61B 5/107* (2013.01); *A61B 5/4547* (2013.01);
(Continued)

(58) Field of Classification Search
None
See application file for complete search history.

(56) References Cited

U.S. PATENT DOCUMENTS 4,823,809 A * 4/1989 Gott, Jr. ............... A61C 19/043
33/514

FOREIGN PATENT DOCUMENTS

JP    2001-061873    3/2001
JP    2002-224148    8/2002
(Continued)

*Primary Examiner* — Matthew Kremer
(74) *Attorney, Agent, or Firm* — The Webb Law Firm

(57) ABSTRACT

The sample attachment level (M) of each tooth is measured in a plurality of tooth samples taken per tooth type from a plurality of teeth extracted as unconservable teeth. A lost periodontal membrane area ($S_L$) is calculated based on the sample attachment level (M) and a total periodontal membrane area (S). A bite force coefficient (B) different according only to each tooth type, which reflects the bite force of each tooth, is found. The relation between the bite force coefficient (B) and a lost periodontal membrane area ($S_{LB}$) at the time of loss of each tooth is statistically processed for each tooth type, and a linear equation showing the relation between the bite force coefficient (B) and the lost periodontal membrane area ($S_{LB}$) at the time of loss of each tooth is prepared by use of the presence of a linear relation between both parameters.

5 Claims, 9 Drawing Sheets

(51) Int. Cl.
　　　*A61C 19/04*　　　(2006.01)
　　　*A61B 10/02*　　　(2006.01)
　　　*A61C 19/05*　　　(2006.01)
　　　*A61B 5/107*　　　(2006.01)

(52) U.S. Cl.
　　　CPC .......... *A61B 5/7278* (2013.01); *A61B 5/7282* (2013.01); *A61B 10/00* (2013.01); *A61B 10/02* (2013.01); *A61C 19/04* (2013.01); *A61C 19/05* (2013.01); *A61C 19/043* (2013.01)

(56) References Cited

FOREIGN PATENT DOCUMENTS

| | | |
|---|---|---|
| JP | 2003-319951 | 11/2003 |
| JP | 2011-072573 | 4/2011 |
| JP | 2011-098047 | 5/2011 |

* cited by examiner (a)

(b)

PERIODONTAL INDEX CREATION METHOD, PERIODONTAL INDEX CREATION APPARATUS, PERIODONTAL INDEX CREATION PROGRAM, AND RECORDING MEDIUM HAVING RECORDS OF PERIODONTAL INDEX CREATION PROGRAM, AND PERIODONTITIS DIAGNOSIS METHOD, PERIODONTITIS DIAGNOSIS APPARATUS, PERIODONTITIS DIAGNOSIS PROGRAM, AND RECORDING MEDIUM HAVING RECORDS OF PERIODONTITIS DIAGNOSIS PROGRAM

CROSS-REFERENCE TO RELATED APPLICATION

This application is the United States national phase of International Application No. PCT/JP2013/070773 filed Jul. 31, 2013, the disclosure of which is hereby incorporated in its entirety by reference.

TECHNICAL FIELD

This invention relates to a periodontal index creation method, a periodontal index creation apparatus, a periodontal index creation program, and a recording medium having records of the periodontal index creation program, and a periodontitis diagnosis method, a periodontitis diagnosis apparatus, a periodontitis diagnosis program, and a recording medium having records of the periodontitis diagnosis program. More specifically, the invention relates to those useful for application to judgment of the necessity for tooth extraction associated with periodontal disease.

BACKGROUND ART

For any disease, it is a basic principle that an index representing the severity of its progression is required. In the treatment of periodontal disease as well as recent tooth implant treatment, the establishment of tooth extraction criteria with high predictivity is desired. Periodontal disease is a disease in which the alveolar bone supporting the teeth is disappearing. Upon complete disappearance of the alveolar bone, a denture inserted with the alveolar ridge as the base becomes unstable. Tooth implant procedure for implantation into the alveolar bone is also unfeasible, thus making it difficult to restore mastication.

At what point in time should a tooth with periodontal disease be judged unconservable? How should the diseased tooth be extracted based on this judgment, with a relatively large amount of the alveolar bone being retained? These are common problems in the treatment of periodontal disease. That is, presenting objective and unerring criteria for tooth extraction is an important, urgent matter.

$S_S/S$ (S=total periodontal membrane area, $S_S$=remaining periodontal membrane area) has been studied since olden days by periodontists throughout the world as one of the diagnostic criteria for diagnosing periodontal disease, and methodologies for producing its values have been discussed variously. One of methods proposed for obtaining such diagnostic criteria comprises tracing an X-P photo on white paper, and measuring the amount of the alveolar bone surrounding the root of the tooth. Such a method, however, has not been successfully evaluated as presenting the same criteria, for causes such that it takes time because it has to trace X-P photos each time they are taken; the amount of X-P irradiation is not necessarily constant for all people; the direction of irradiation is not constant; and the bone densities of subjects are varied.

An improvement in these problems is a method which comprises taking pictures from a plurality of directions using computed tomography (CT) to reproduce three-dimensional periodontal tissue by use of a computer, thereby measuring $S_S/S$. Periodontal disease screening generally done in periodontal treatment is performed dozens of times during a lifetime. In view of this fact, the above method utilizing CT gives an enormous amount of radiation exposure. Furthermore, this method is feasible as a method for experiments on a single subject such as human experimentation or animal experiments. However, under situations where most countries have only several CT devices/country, it is difficult to diagnose periodontal diseases on a wide scale by use of that method, except in an environment in which CT is in relatively widespread use. Besides, even if the $S_S/S$ could be accurately calculated, this index itself does not serve as a figure, which singly presents objective criteria, like other diagnostic methods such as the depth of a pocket. The above method involves the inconvenience that a diagnosis has to be made globally in consideration of results obtained by other diagnostic methods.

Patent Document 1 and Patent Document 2 are publicly known as prior art documents disclosing methods for examination of periodontal disease which comprise using a value, calculated as the ratio ($S_C/S$) of the remaining root surface area ($S_C$) supporting the current tooth to the total root surface area (S) supporting the healthy tooth, as a root surface area index, and examining the state of progression of periodontal disease based on this index.

PRIOR ART DOCUMENTS

Patent Documents

Patent Document 1: JP-A-2011-98047
Patent Document 2: JP-A-2011-72573

The root surface area index ($S_C/S$) disclosed by Patent Documents 1 and 2 as the index cannot serve as a single index representing tooth extraction criteria as discussed earlier. In addition, the root surface area index ($S_C/S$) is predicated on image processing which images a tooth by dental X-rays.

Thus, the root surface area index ($S_C/S$) poses no problems in the medical settings of advanced countries equipped with various instruments for medical examinations. However, the root surface area index ($S_C/S$) arouses the problem that its application is difficult in developing countries, etc. which are not fully equipped with X-ray imaging devices.

Furthermore, the root surface area index ($S_C/S$), even when accurately calculated, is unable to become, singly, a highly reliable index.

The present invention has been accomplished in the light of the above-mentioned problems with the conventional technologies. It is an object of the present invention to provide a method for creating a periodontal index capable of presenting highly reliable tooth extraction criteria by a simple examination, an apparatus for creating the periodontal index, a program for creating the periodontal index, and a recording medium having records of the periodontal index creation program; and a method for diagnosing periodontitis, an apparatus for diagnosing periodontitis, a program for diagnosing periodontitis, and a recording medium having records of the periodontitis diagnosis program.

SUMMARY OF THE INVENTION

As discussed above, even when the root surface area index ($S_C/S$) in customary use is accurately calculated, this index, alone, cannot become a highly reliable index. A probable cause would be as follows: For example, two kinds of teeth with ($S_C/S$)=1/2 are assumed, as shown in FIGS. 1(a) and 1(b). One of the teeth is the mandibular first tooth (see FIG. 1(a)), and the other tooth is the mandibular seventh tooth (see FIG. 1(b)). Both teeth shown in FIGS. 1(a), 1(b) have ($S_C/S$)=1/2. A clinical diagnosis of periodontal disease, however, shows that the mandibular first tooth shown in FIG. 1(a) has a satisfactory prognosis, while the mandibular seventh tooth shown in FIG. 1(b) has a poor prognosis indicative of a severe periodontal disease.

As discussed above, a clinical diagnosis of periodontal disease cannot be made based on the conventional root surface area index ($S_C/S$) alone. The root surface area index ($S_C/S$) is of some help toward making a diagnosis, but an overall diagnosis has to be performed using various other diagnostic methods.

The reason why clinical diagnosis on periodontal disease produces different diagnostic results although the root surface area index ($S_C/S$) is the same (for example ½) will be considered. For this purpose, it is necessary, first of all, to know the clinical phenomena of periodontal disease.

In patients with periodontal diseases who received periodontal treatment and entered the maintenance phase, 221 teeth had to be extracted because of a poor prognosis. These 221 teeth were classified by the type of the tooth on each of the right and left sides of the upper and lower jaws, and subjected to observation. The attachment level at the time of dental loss was not different between the upper jaw and the lower jaw, nor between the right side and the left side. The attachment level was found to be different according to the type of the tooth.

The attachment level refers to the extent of the periodontal supporting tissue, and includes the level of the alveolar bone as an example. The mandibular first tooth in FIG. 1(a) will be taken as an example for observation. The attachment level M is taken as the distance from the cementoenamel junction CEJ, which is the boundary between the crown 1 having a surface composed of enamel and the root 2 having a surface composed of cementum, to the lowermost site with a loss of the periodontal membrane along the tooth surface. The periodontal membrane which has been lost is called the lost periodontal membrane 3A, and the area of the lost periodontal membrane 3A along its entire circumference in the root 2 is called the lost periodontal membrane area $S_L$. On the other hand, the periodontal membrane remaining in the alveolar bone 4 is called the remaining periodontal membrane 3B, and the area of the remaining periodontal membrane 3B along its entire circumference in the root 2 is called the remaining periodontal membrane area $S_S$.

As mentioned earlier, the distributions of the 221 teeth, which had to be extracted because of a poor prognosis, on the right and left sides of the upper and lower jaws are shown in Table 1. The attachment levels of the respective teeth are shown in Table 2, and a bar graph of the attachment levels of the respective teeth is shown in FIG. 2.

TABLE 1

Number of test teeth by tooth type (n = 221)

| | | | | | | Upper jaw | | | | | | |
|---|---|---|---|---|---|---|---|---|---|---|---|---|
| Right side | | | | | | | | | | | | Left side |
| 8 | 8 | 14 | 7 | 10 | 8 | Number of samples | 8 | 10 | 7 | 13 | 8 | 9 |
| 7 | 6 | 54 | 3 | 2 | 1 | Tooth type | 1 | 2 | 3 | 45 | 6 | 7 |
| 10 | 10 | 13 | 6 | 8 | 8 | Number of samples | 7 | 9 | 6 | 14 | 9 | 11 |
| | | | | | | Lower jaw | | | | | | |

TABLE 2

Attachment level values by tooth type when teeth were lost

| | | | | | | Upper jaw | | | | | | |
|---|---|---|---|---|---|---|---|---|---|---|---|---|
| Right side | | | | | | | | | | | | Left side |
| 7.2 | 6.5 | 8.3 | 7.3 | 8.0 | 10.5 | Attachment level | 8.0 | 11.0 | 10.0 | 6.4 | 6.3 | 7.5 |
| 7 | 6 | 54 | 3 | 2 | 1 | Tooth type | 1 | 2 | 3 | 45 | 6 | 7 |
| 4.0 | 5.6 | 6.9 | 9.5 | 9.6 | 10.5 | Attachment level | 9.5 | 10.2 | 7.8 | 5.9 | 6.5 | 4.3 |
| | | | | | | Lower jaw | | | | | | |

The cause of occurrence of the differences in attachment level among the respective teeth that had to be extracted because of a poor prognosis was investigated, and found to be related to bite force. In detail, the periodontal membrane enclosing the circumference of the root is a connective tissue, which connects the cementum on the surface of the root and the surrounding alveolar bone, and supports and holds the tooth. When the periodontal membrane was destroyed and lost owing to periodontal disease, its area on the surface of the root was found to parallel the bite force exerted when chewing or gritting the teeth. That is, the type of tooth, which is nearer the temporomandibular joint and undergoes stronger bite force, suffers from a greater loss in the area of the periodontal membrane because of periodontal disease. In other words, the anterior tooth and the posterior tooth with ($S_C/S$)=½ each have a half periodontal membrane area remaining, but the remaining periodontal membrane is lost earlier in the posterior tooth, so that the posterior tooth has a poor prognosis as compared with the anterior tooth.

Under these circumstances, the present invention, which obtains an index appropriately incorporating the action of bite force, has been arrived at, with the expectation that an index accurately reflecting the severity of periodontal disease may be obtainable by taking bite force into consideration.

A first aspect of the present invention, designed to attain the above object based on such an expectation, is a periodontal index creation method, comprising:

a measurement step of using a plurality of teeth extracted, because they are judged to be unconservable, as objects, and measuring a sample attachment level, which is a dimension ranging from the cementoenamel junction of each tooth or the crown margin of the tooth with a veneer crown to a lowermost site of a submarginal dental calculus deposited portion of the tooth in a plurality of samples taken for each tooth type from the teeth;

a periodontal membrane area computation step of finding the lost periodontal membrane area of each tooth based on the total periodontal membrane area of each tooth and the sample attachment level;

a bite force coefficient computation step of finding a bite force coefficient for each tooth, with the cusp of each tooth being taken as the point of action of a lever and the condyle of the temporomandibular joint as the fulcrum of the lever, based on the ratio between the distance from the cusp to the condyle and the distance from a specific reference tooth giving a reference position to the condyle, and the ratio between the length of the reference tooth and the length of each tooth, the distances and the lengths being given preliminarily;

a straight line preparation step of preparing a bite force-lost periodontal membrane straight line which is a linear equation showing the relationship between the bite force coefficient and the lost periodontal membrane area, by utilizing the fact that there is a linear relationship between the value of the bite force coefficient different according to the tooth type alone and the value of the lost periodontal membrane area when statistically processing the relationship between the bite force coefficient and the lost periodontal membrane area for each type of tooth;

a lost periodontal membrane area detection step of finding an at-time-of-loss lost periodontal membrane area, which is a lost periodontal membrane area at the time of loss of each tooth, corrected in consideration of the bite force coefficient, based on the bite force-lost periodontal membrane straight line obtained in the straight line preparation step; and an at-time-of-loss periodontal index computation step of calculating (at-time-of-loss remaining periodontal membrane area/total periodontal membrane area)×100(%) as a periodontal index at the time of loss of each tooth, based on an at-time-of-loss remaining periodontal membrane area determined by subtracting the at-time-of-loss lost periodontal membrane area from the total periodontal membrane area.

The periodontal membrane supports and holds the tooth, and it has been found that the area of the periodontal membrane on the root surface destroyed and lost by periodontal disease parallels the bite force exerted when chewing or gritting the teeth. Based on this finding, the new concept, bite force coefficient, is introduced according to the present aspect. This aspect also utilizes the findings that the lost periodontal membrane area at the time of loss of each tooth, which is found in association with the sample attachment level, has a strong correlation with the bite force coefficient, the correlation being expressed by a linear function, and that the lost periodontal membrane area at the time of tooth loss can be represented as incorporating the bite force coefficient. By utilizing these findings, it is possible to prepare the periodontal index which is the proportion of the remaining periodontal membrane area taking the bite force coefficient into consideration, at the time of loss of each tooth, to the total periodontal membrane area.

Consequently, it becomes possible to obtain the at-time-of-loss periodontal index which is the proportion of the remaining periodontal membrane area taking the bite force coefficient into consideration, at the time of loss of each tooth, a parameter needed in preparing a new objective index unerringly reflecting the severity of progression of periodontitis.

A second aspect of the present invention is the periodontal index creation method described in the first aspect, further comprising:

a periodontal index creation step of creating a periodontal index which is the proportion of a remaining periodontal membrane area taking the bite force coefficient of each tooth into consideration to the total periodontal membrane area, the periodontal index being represented by a line passing through three points representing a value of 100 being a periodontal index when all of the periodontal membrane remains, a value of 0 being a periodontal index when all of the periodontal membrane is lost, and a value being the at-time-of-loss periodontal index as the periodontal index at the time of loss of each tooth.

The periodontal index obtained by the present aspect serves as an objective index unerringly reflecting the severity of progression of periodontitis, and is useful as an index presenting tooth extraction criteria objectively. That is, according to the present aspect, the periodontal index as an absolute index to the health of a tooth conformed to the clinical status of periodontal disease with higher accuracy can be easily provided.

A third aspect of the present invention is the periodontal index creation method described in the first or second aspect, wherein the periodontal membrane area computation step includes a pseudo-root preparation step of preparing a pseudo-root from which the total periodontal membrane area of each tooth can be calculated quantitatively; a total periodontal membrane area computation step of calculating the total periodontal membrane area based on the pseudo-root; and a lost periodontal membrane area computation step of calculating the lost periodontal membrane area of the tooth based on the total periodontal membrane area and the sample attachment level.

According to the present aspect, the preparation of the pseudo-root enables the total periodontal membrane area, the lost periodontal membrane area, and the remaining periodontal membrane area to be found easily and unerringly as areas based on the pseudo-root.

A fourth aspect of the present invention is the periodontal index creation method described in the third aspect, wherein the pseudo-root in the periodontal membrane area computation step is created by regarding the root of a single rooted tooth as a single conical body, regarding the roots of a double rooted tooth as an aggregate of a plurality of conical bodies, and taking the diameter (R) of the bottom of the conical body as the diameter of the cementoenamel junction (CEJ) of the root, the height (H) of the conical body as the length of the root, and the ridge line length (C) of the cone of the conical body as the ridge line length of the root, wherein the total periodontal membrane area is computed based on Equation (1), the remaining periodontal membrane area is computed based on Equation (2), and the lost periodontal membrane area is found by performing a predetermined computation using Equation (3):

[Equation 1]
the lateral area of the pseudo-root conical body is regarded as the total periodontal membrane area.
H: root length
C: root ridge line length
R: root CEJ diameter
r: CEJ root radius
Since $S = \pi rc$,
$r = \dfrac{R}{2}$ and
$c = \sqrt{r^2 + H^2}$ are substituted into this equation to obtain the following total periodontal membrane area $S$:

$$S = \frac{\pi}{2} R \sqrt{\frac{R^2}{4} + H^2} \tag{1}$$

[Equation 2]

$$S_s = \frac{\pi}{2}\left(R - \frac{RM}{\sqrt{\dfrac{R^2}{4} + H^2}}\right)\left(\sqrt{\frac{R^2}{4} + H^2} - M\right) \tag{2}$$

[Equation 3]

$$S_L = \frac{\pi}{2}\left\{R\sqrt{\frac{R^2}{4} + H^2} - \left(R - \frac{RM}{\sqrt{\dfrac{R^2}{4} + H^2}}\right)\left(\sqrt{\frac{R^2}{4} + H^2} - M\right)\right\} \tag{3}$$

According to the present aspect, the pseudo-root can be prepared easily and unerringly, and the total periodontal membrane area, the remaining periodontal membrane area, and the lost periodontal membrane area based on this pseudo-root can be found easily and unerringly.

A fifth aspect of the present invention is the periodontal index creation method described in the first or second aspect, wherein
the bite force coefficient is computed based on Equation (4).

[Equation 4]

$$\text{Bite force coefficient } B = \frac{TP}{AQ} \tag{4}$$

In Equation (4) indicated above,
T: distance from occlusion site of each tooth type to condyle of temporomandibular joint
A: distance from incisal margin of mandibular anterior first tooth to condyle of temporomandibular joint (reference value)
P: distance from incisal vestibular surface angle of mandibular anterior first tooth to root apex (reference value)
Q: length of tooth (distance from site of occlusal contact to farthest root apex)

According to the present aspect, a concrete and unerring bite force coefficient can be provided.

A sixth aspect of the present invention is the periodontal index creation method described in the second aspect, wherein
when the remaining periodontal membrane area is set for a horizontal axis and the periodontal index is set for a vertical axis, the periodontal index creation step comprises:
drawing a straight line connecting two points representing 100 which is the periodontal index when all the periodontal membrane remains, and 0 which is the periodontal index when all the periodontal membrane is lost;
plotting the periodontal index at the time of loss, and moving the straight line in parallel so as to become a straight line passing through the plotted point;
preparing a periodontal index curve, which passes through the two points representing the periodontal indices of 0 and 100, and contacts the parallel-moved straight line only at the plotted point, and using a point on the periodontal index curve corresponding to a specific remaining periodontal membrane area as a periodontal index corresponding to the specific remaining periodontal membrane area.

According to the present aspect, a desired periodontal index taking bite force into consideration can be obtained utilizing the periodontal index curve, simply by specifying the remaining periodontal membrane area.

A seventh aspect of the present invention is a periodontal index creation apparatus, comprising:
a computation unit which
receives input of sampling data representing measured values of a plurality of samples taken for each tooth type from a plurality of teeth extracted because they are judged to be unconservable, the measured values being obtained by measuring a sample attachment level, which is a dimension ranging from the cementoenamel junction of each tooth or the crown margin of the tooth with a veneer crown to a lowermost site of a submarginal dental calculus deposited portion of the tooth in the samples, and
executes processings of the periodontal membrane area computation step, the bite force coefficient computation step, the lost periodontal membrane area detection step, and the at-time-of-loss periodontal index computation step in the periodontal index creation method described in the first aspect, thereby creating the periodontal index at the time of loss of each tooth.

According to the present aspect, the periodontal index at the time of loss of each tooth can be automatically obtained simply by inputting the sampling data on the sample attachment level to the computation unit.

The above feature can contribute to the creation of the periodontal index which is an absolute index to the health of a tooth conformed to the clinical status of periodontal disease with higher accuracy.

An eighth aspect of the present invention is the periodontal index creation apparatus described in the seventh aspect, wherein
the computation unit is adapted to execute processings of the periodontal index creation step in the periodontal index creation method described in the second or sixth aspect to create a periodontal index further.

According to the above aspect, the periodontal index, which is an absolute index to the health of a tooth conformed highly accurately to the clinical status of periodontal disease, can be created automatically.

A ninth aspect of the present invention is a periodontal index creation program, comprising:
allowing the periodontal index creation apparatus described in the seventh aspect to execute processings of the periodontal membrane area computation step, the bite force coefficient computation step, the lost periodontal membrane area detection step, and the at-time-of-loss periodontal index computation step in the periodontal index creation method described in any of the first to fifth aspects.

According to the present aspect, the periodontal index creation apparatus described in the seventh aspect can be allowed to execute the processings of the predetermined steps in the periodontal index creation method described in the first aspect. The data of the periodontal index creation program can be provided satisfactorily to the periodontal index creation apparatus even via a telecommunications line such as the Internet. Thus, the periodontal index creation program is downloaded from the Internet or the like to a personal computer, whereby the general-purpose personal computer can be allowed to function as a periodontal index creation apparatus for creating the above periodontal index BPI.

A tenth aspect of the present invention is a periodontal index creation program, comprising:

allowing the periodontal index creation apparatus described in the eighth aspect to execute processings of the periodontal index creation step in the periodontal index creation method described in the second or sixth aspect.

According to the present aspect, the processings of the predetermined steps in the periodontal index creation method described in the second or sixth aspect, including the processings of the periodontal index creation step, can be satisfactorily executed by the periodontal index creation apparatus described in the seventh aspect.

An eleventh aspect of the present invention is a recording medium having records of the periodontal index creation program described in the ninth aspect which can be read by the periodontal index creation apparatus described in the seventh aspect.

According to the present aspect, distribution or the like of the periodontal index creation program described in the ninth aspect can be carried out satisfactorily. As a result, hardware such as a personal computer, if any, is installed with the periodontal index creation program, whereby it can easily function anywhere as an apparatus for creating an at-time-of-loss periodontal index based on the lost periodontal membrane area at the time of loss of each tooth.

A twelfth aspect of the present invention is a recording medium having records of the periodontal index creation program described in the tenth aspect which can be read by the periodontal index creation apparatus described in the eighth aspect.

According to the present aspect, distribution or the like of the periodontal index creation program described in the tenth aspect can be carried out satisfactorily. As a result, the periodontal index creation program is installed on hardware such as a personal computer, if any, thereby enabling the hardware to perform the function of an apparatus for creating a periodontal index with ease and at any place.

A thirteenth aspect of the present invention is a periodontitis diagnosis method, comprising:

measuring the attachment level of a specific tooth, as an object of diagnosis, thereby detecting the measured attachment level;

calculating the remaining periodontal membrane area ($S_S$) of the tooth as the object of diagnosis based on the measured attachment level; and creating the periodontal index (BPI) of the specific tooth corresponding to the remaining periodontal membrane area ($S_S$) by the periodontal index creation step described in the second or sixth aspect.

According to the present aspect, simply by obtaining data on the measured attachment level of the specific tooth as the object of diagnosis, it becomes possible to determine a periodontal index taking bite force, different according to the type of tooth, into consideration, thereby obtaining unerring and objective tooth extraction criteria for periodontitis treatment. Thus, appropriate treatment of periodontitis can be conducted.

A fourteenth aspect of the present invention is a periodontitis diagnosis apparatus, comprising:

a computation unit which receives input of measured data representing the measured attachment level of the specific tooth measured in the thirteenth aspect, calculates the remaining periodontal membrane area of the tooth as the object of diagnosis based on the measured attachment level, and further executes processings of the periodontal index creation step described in the second or sixth aspect to create the periodontal index of the specific tooth corresponding to the remaining periodontal membrane area.

According to the present aspect, simply by inputting data on the measured attachment level obtained by measuring the attachment level of the specific tooth as the object of diagnosis, a periodontal index taking bite force different according to the type of tooth into consideration can be determined easily and automatically. As a result, unerring and objective tooth extraction criteria for periodontitis treatment can be easily obtained. Thus, appropriate treatment of periodontitis can be conducted easily and promptly. The diagnosis apparatus can be prepared suitably by a personal computer or the like. If data on the measured attachment level of the specific tooth are obtained, therefore, the resulting diagnosis apparatus can be used as an excellently versatile diagnostic apparatus which can convey the data easily to any place. Hence, it can be conducive to diagnosis providing objective tooth extraction criteria associated with periodontitis, as a compact and highly versatile apparatus. That is, compared with an X-ray device hitherto used in this type of diagnosis, the apparatus can be dramatically downsized, is dramatically improved in portability, and is easy to handle. Furthermore, the amount of X-ray exposure associated with treatment or the like can be rendered as small as possible.

A fifteenth aspect of the present invention is a periodontitis diagnosis program, comprising:

allowing the periodontitis diagnosis apparatus described in the fourteenth aspect to perform processings which calculate the remaining periodontal membrane area of the tooth as the object of diagnosis based on the measured attachment level in the periodontitis diagnosis method described in the thirteenth aspect; and create the periodontal index of the specific tooth corresponding to the remaining periodontal membrane area by the periodontal index creation step described in the second or sixth aspect.

According to the present aspect, a predetermined periodontal index can be automatically generated, and allowed to contribute to easy and prompt treatment of periodontitis. The data of the periodontitis diagnosis program can be provided satisfactorily to the periodontal index creation apparatus even via a telecommunications line such as the Internet. Thus, the periodontitis diagnosis program is downloaded from the Internet or the like to a personal computer, whereby the personal computer can be allowed to function as a diagnostic apparatus for periodontitis.

A sixteenth aspect of the present invention is a recording medium having records of the periodontitis diagnosis program described in the fifteenth aspect which can be read by the periodontitis diagnosis apparatus described in the fourteenth aspect.

According to the present aspect, distribution or the like of the above program can be carried out satisfactorily. As a result, if there is general-purpose inexpensive hardware such as a personal computer, without an expensive medical instrument such as an X-ray imaging device, the hardware having the program installed thereon can easily function anywhere as a periodontal index creation apparatus.

With the present invention, based on a strong correlation between the lost periodontal membrane area or the remaining periodontal membrane area and bite force, a novel periodontal index is found by utilizing a bite force-lost periodontal membrane straight line obtained by an equation representing the relation between both parameters. This periodontal index is calculated under clinical rules on periodontal disease, and uses a corrected remaining periodontal membrane area or a corrected lost periodontal membrane area corrected in consideration of bite force. Thus, the periodontal index provides an absolute evaluation of the health of tooth conformed to the clinical status of periodontal disease. Because of the course of derivation of the periodontal index, in particular, it serves as a highly predictive index unerringly representing the severity of progression of periodontitis which shows in detail the situations around the time of loss of the tooth.

According to the present invention, moreover, the measurement of the attachment level at the predetermined site (lowermost site) of the diseased tooth in clinical practice on periodontal disease enables evaluation of periodontal disease to be made upon entry into BPI software, without adopting complicated instruments or procedures. Thus, there are no errors due to the drawbacks of the instruments, nor any errors in judgment between operators. Consequently, the evaluation of periodontal disease can be made at the same level throughout the world and with the passage of time. Hence, the present invention can provide a useful method for evaluation of periodontal disease in clinical practice on patients with periodontal disease as well as in clinical trial of subjects with periodontal disease.

DETAILED DESCRIPTION OF THE INVENTION

Figure 1:
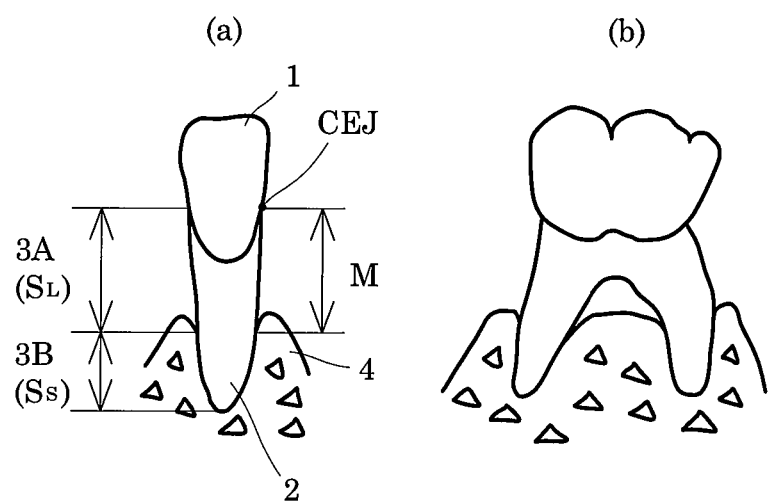
FIGS. 1(a), 1(b) are schematic views of teeth, showing a single rooted tooth (FIG. 1(a)) and a double rooted tooth (FIG. 1(b)).
Figure 2:
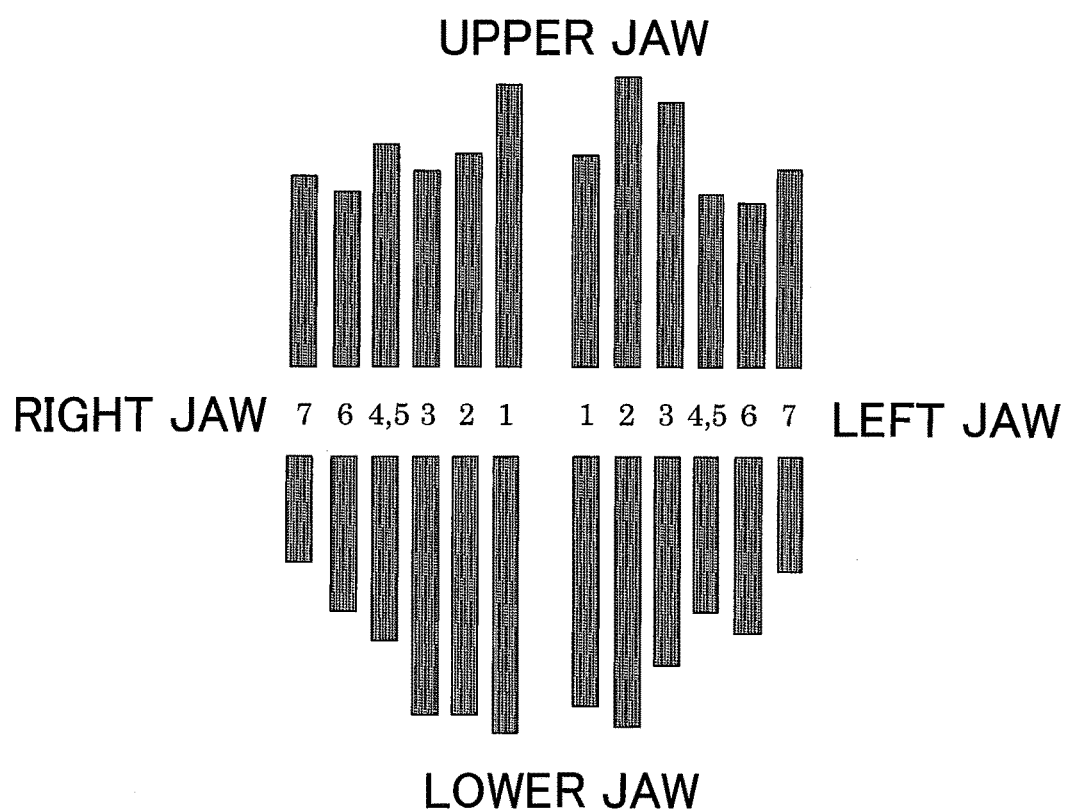
FIG. 2 is a graph showing the attachment levels of samples of respective tooth types extracted as unconservable teeth because of periodontitis.

An embodiment of the present invention will be described in detail hereinbelow by reference to the accompanying drawings.

<Periodontal Index Creation Method and Periodontitis Diagnosis Method>

In the periodontal index creation method according to the present embodiment, a plurality of teeth (221 teeth in the present embodiment) extracted as unconservable teeth are selected as objects, and a plurality of samples are taken from them for each type of tooth (see Table 1). The attachment level, which is a dimension ranging from the cementoenamel junction of each tooth or the crown margin of the tooth with a veneer crown to the lowermost site of a submarginal dental calculus deposited portion of the tooth, is measured in each of these samples. The measurements are performed in units of millimeters at six locations per tooth (i.e., buccomesial, buccomeso, buccodistal, linguomesial, linguomeso, and linguodistal). The measured attachment levels are taken as the sample attachment levels of the first to seventh teeth on each of the right and left sides of the upper jaw and the first to seventh teeth on each of the right and left sides of the lower jaw. As these sample attachment levels, the greatest values obtained by the measurements of the attachment levels of the respective teeth are adopted. The values of the lowermost sites of the submarginal dental calculus deposited portions of the respective teeth were classified by the type of tooth (for the premolar portion, data on the fourth and fifth teeth were put together because of anatomical difficulty), and the average values were obtained (see Tables 1 and 2). Concretely, the average values of the attachment levels (for the respective types of teeth on the right and left sides of the upper and lower jaws) were calculated from the measured values of the attachment levels obtained in the respective teeth. The resulting values were subjected to two-way factorial analysis of variance to find the sample attachment levels M.

The results are shown in the above-mentioned Table 2. As will become clear by reference to this table, the maximum value of the sample attachment level M at the time of loss of tooth was 11.0 mm of the second tooth on the left side of the upper jaw, and its minimum value was 4.0 mm of the seventh tooth on the right side of the lower jaw, indicating that the sample attachment level M tended to be of high value in the anterior teeth, and of low value in the posterior teeth. Statistical analysis of the data showed no differences between the upper jaw and the lower jaw or between the right side and the left side in the average values, classified by the type of tooth, of the sample attachment level M at the time of loss of tooth, as will be discussed later in detail. However, differences in the type of tooth were noted among the first to seventh teeth (P=0.0014).

Next, pseudo-roots permitting the quantitative calculation of the total periodontal membrane areas S of the respective sample teeth are prepared. Moreover, calculations are made of the total periodontal membrane area S of each tooth based on the pseudo-root, the remaining periodontal membrane area $S_S$ of each tooth based on the sample attachment level M, and the lost periodontal membrane area $S_L$ which is the difference between the total periodontal membrane area S and the remaining periodontal membrane area $S_S$.

Concretely, the following pseudo-root is prepared, and the following predetermined computations are performed based on the resulting pseudo-root to calculate the total periodontal membrane area S, the remaining periodontal membrane area $S_S$, and the lost periodontal membrane area $S_L$.

First, a pseudo-root which enables the periodontal membrane area to be quantitatively calculated is prepared. Concretely, the root of a single rooted tooth is regarded as a conical body, and the roots of a double rooted tooth are regarded as an aggregate of a plurality of conical bodies. Then, the total periodontal membrane area S which is the entire surface area of the root, the lost periodontal membrane area $S_L$ which is the surface area of the periodontal membrane lost by periodontitis, and the remaining periodontal membrane area $S_S$ which is the surface area of the unlost periodontal membrane are calculated from the lateral area of the conical body. Such a series of computing steps will be described in detail based on FIGS. 3(a) to 3(d).

1) A pseudo-root is prepared.

a) A single rooted tooth as shown in FIG. 1(a)

Figure 3:
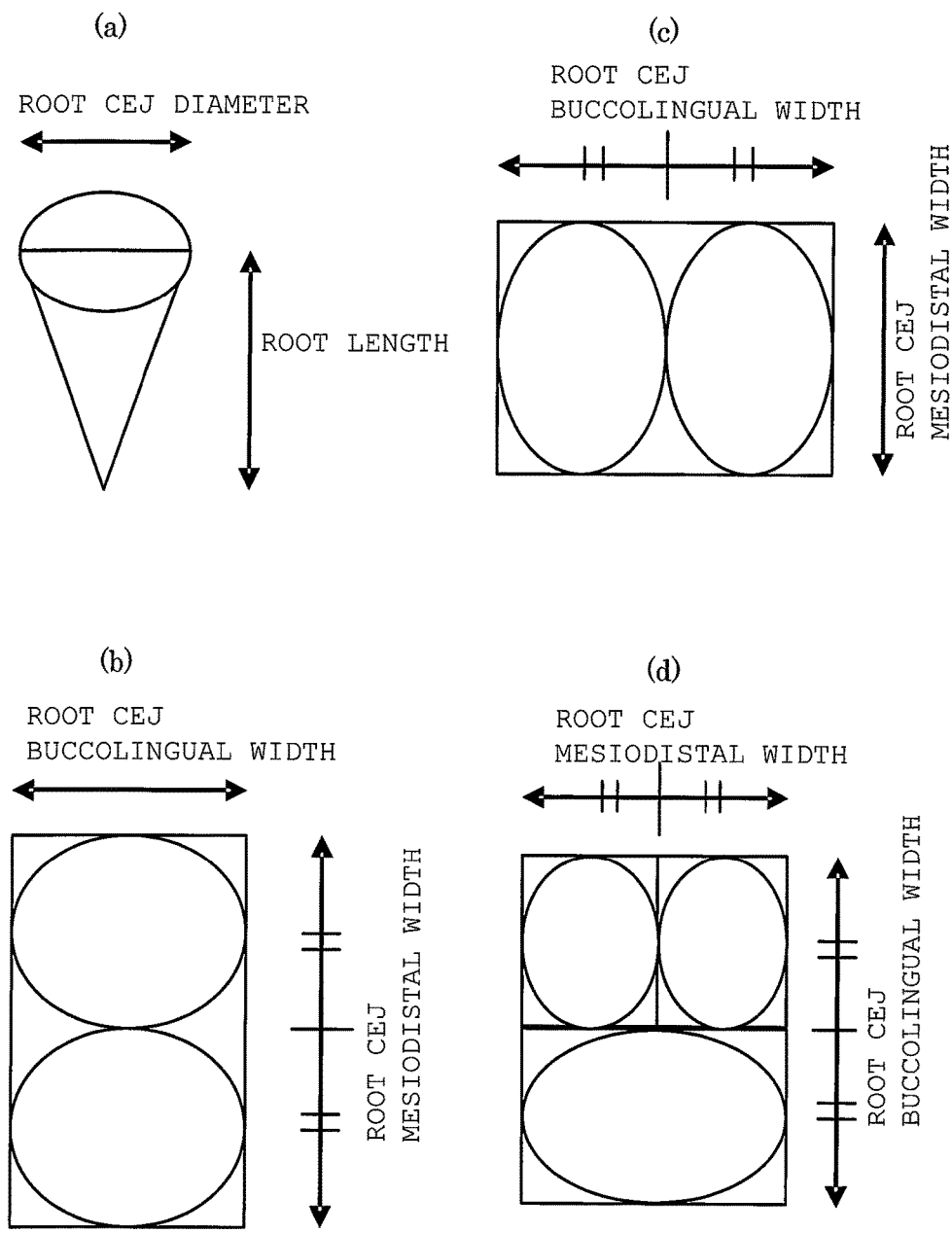
FIGS. 3(a) to 3(d) are explanation drawings schematically showing various pseudo-roots.

As shown in FIG. 3(a), the diameter of the root at the cementoenamel junction (will hereinafter be referred to as CEJ) (the root will hereinafter be called the CEJ root) is represented by the diameter of the bottom of the conical body, and the length of the root is represented by the height of the conical body. Since the value is different between the mesiodistal side and the buccolingual side at the CEJ root, the average of the values on both sides is calculated.

b) A double rooted tooth as shown in FIG. 1(b), like the fourth and fifth teeth of the upper jaw As shown in FIG. 3(b), the tooth is regarded as having two conical bodies composed of two roots on the buccolingual side.

c) A double rooted tooth, like the sixth and seventh teeth of the lower jaw

As shown in FIG. 3(c), the tooth is regarded as having two conical bodies composed of two roots on the mesiodistal side.

d) A double rooted tooth, like the sixth and seventh teeth of the upper jaw

As shown in FIG. 3(d), the tooth is regarded as having three conical bodies composed of a conical body on the palatal side having a half of the width on the buccolingual side, and two conical bodies on the buccal side having a half of the mesiodistal width.

e) The tooth shown in each of FIGS. 3(b) to 3(d), like the single rooted tooth shown in FIG. 3(a), has the value which, at the CEJ root, is different between the mesiodistal side and the buccolingual side. Thus, the average of the values on both sides is calculated.

f) The CEJ root is located nearer the crown on the mesiodistal side of the root, and nearer the apex of the root on the buccolingual side of the root. Thus, the average of the root length ranging from the CEJ root of the mesiodistal portion to the apex of the root, and the root length ranging from the CEJ root of the buccolingual portion to the apex of the root is used as the length of the root.

g) The fourth, fifth, sixth and seventh multi-rooted teeth of the upper jaw, and the sixth and seventh multi-rooted teeth of the lower jaw are different in the length of the root in the mesiodistal roots and the buccolingual roots. Thus, the roots of these teeth are regarded as aggregates of conical bodies with different heights.

h) The average values taken from Yasuhiko Kamijou, "Anatomy of Permanent Teeth in the Japanese (literally)", published by Anatome Co., Ltd., the book on the anatomy of teeth in the Japanese, were used as the mesiodistal width, the buccolingual width, and the root length at the site of the root CEJ.

i) The diameters and root lengths (mm) of the pseudo-roots classified by the type of the tooth, which were calculated based on a) to h) above, are shown in Table 3.

TABLE 3

Diameters and root lengths (mm) of pseudo-roots classified by type of tooth

| | | | | | | |
|---|---|---|---|---|---|---|
| Root length H | 11.8 | 12.1 | 15.6 | B root 12.5 | BM root 11.5 BD root 11.5 P root 12.5 | BM root 11.6 BD root 11.6 P root 12.3 |
| Diameter R | 6.5 | 5.2 | 7.0 | B root 4.4 P root 4.4 | BM root 4.2 BM root 4.2 P root 6.0 | BM root 3.7 BM root 3.7 P root 4.8 |
| Tooth type | 1 | 2 | 3 | 45 | 6 | 7 |
| Diameter R | 4.9 | 5.2 | 6.0 | 6.1 | M root 6.8 D root 6.8 | M root 5.8 D root 5.8 |
| Root length H | 11.2 | 11.5 | 14.0 | 13.2 | M root 12.2 D root 12.8 | M root 11.9 D root 12.2 |

R: Diameter of pseudo-root CEJ (average of mesiodistal width and buccolingual width) (mm)
H: Length of pseudo-root (average of length from mesiodistal CEJ to apex of root and length from buccolingual CEJ to apex of root) (mm)
B: Buccal
P: Palatal
BM: Buccomesial
BD: Buccodistal
M: Mesial
D: Distal 2) The total periodontal membrane area S is calculated from the pseudo-root.

The lateral area of the conical body of the pseudo-root is regarded as the total periodontal membrane area S. Assuming in FIG. 4(a) that H is the length of the root, C is the ridge line length of the root, R is the diameter of the CEJ root, and r is the radius of the CEJ root, then the total periodontal membrane area S is expressed as $S=\pi rC$.

By substituting $r=R/2$ and $C=SQRT(r^2+H^2)$ into the above equation, the total periodontal membrane area S is given by Equation (5).

[Equation 5]

$$S = \frac{\pi}{2}R\sqrt{\frac{R^2}{4} + H^2} \quad (5)$$

3) The remaining periodontal membrane area $S_S$ and the lost periodontal membrane area $S_L$ are calculated from the pseudo-root.

Figure 4:
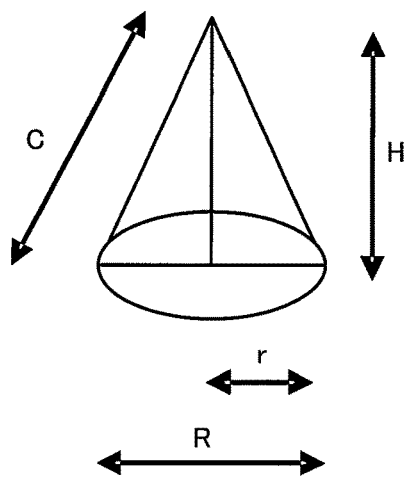
FIGS. 4(a), 4(b) are explanation drawings for illustrating the dimensions of various parts in preparing a pseudo-root of a single rooted tooth regarded as a conical body.
Figure 4:
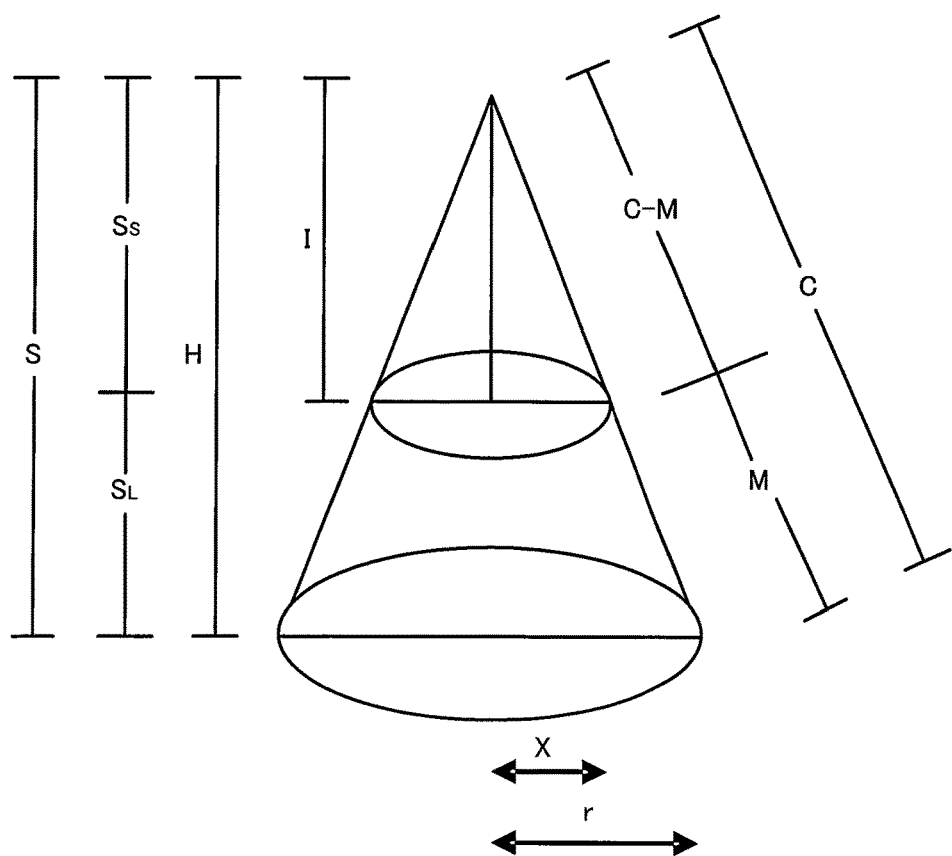

In FIG. 4(b), M, S, $S_S$, $S_L$ and X are defined as follows:

M: maximum sample attachment level (mm) of measured values at six measured points S: total periodontal membrane area (mm$^2$)

$S_S$: remaining periodontal membrane area (mm$^2$)

$S_L$: lost periodontal membrane area (mm²)

X: radius of remaining root (mm)

Thus, the remaining periodontal membrane area $S_S$ is expressed as $S_S = \pi X(C-M)$.

The following values are substituted into the above equation of $S_S$ to obtain Equation (6).

by the type of the tooth at the time of loss of each tooth, which are shown in Table 1, are entered into Equations (5), (7) and (8) to calculate the total periodontal membrane area S, the remaining periodontal membrane area $S_S$, and the lost periodontal membrane area $S_L$ of the root of each tooth type at the time of loss of the tooth. The results are shown in Table 4.

TABLE 4

Total periodontal membrane area (S), remaining periodontal membrane area ($S_S$), and lost periodontal membrane area ($S_L$) of root of each tooth type at time of loss of tooth (unit: mm²)

| 7 | 6 | 5 | 4 | 3 | 2 | 1 type of tooth | 1 | 2 | 3 | 4 5 | 6 | 7 |
|---|---|---|---|---|---|---|---|---|---|---|---|---|
| 193.4 | 211.7 | 154.4 | 123.9 | 88.5 | 122.4 | $S_L$ | 110.0 | 99.8 | 151.1 | 132.6 | 207.6 | 198.1 |
| 37.6 | 50.9 | 21.0 | 51.9 | 12.6 | 2.5 | $S_S$ | 15.0 | 1.3 | 24.7 | 43.1 | 55.0 | 33.1 |
| 231.0 | 262.6 | 175.4 | 175.8 | 101.1 | 124.9 | S | 125.0 | 101.1 | 175.8 | 175.7 | 262.6 | 231.2 |
| 225.9 | 276.7 | 129.9 | 135.0 | 96.3 | 88.2 | S | 88.3 | 96.4 | 135.0 | 129.9 | 276.7 | 226.3 |
| 103.6 | 89.2 | 31.3 | 15.3 | 3.3 | 0.6 | $S_S$ | 2.6 | 1.8 | 28.0 | 41.4 | 68.7 | 96.3 |
| 122.3 | 187.5 | 98.6 | 119.7 | 93.0 | 87.6 | $S_L$ | 85.7 | 94.6 | 107.0 | 88.5 | 208.0 | 130.0 |

[Equation 6]

$$I = H - \frac{HM}{C}$$

$$C = \sqrt{\frac{R^2}{4} + H^2}$$

$$X = \sqrt{(C-M)^2 - I^2} = \sqrt{\left(\sqrt{\frac{R^2}{4}+H^2} - M\right)^2 - \left(H - \frac{HM}{\sqrt{\frac{R^2}{4}+H^2}}\right)^2}$$

(6)

Thus, the remaining periodontal membrane area $S_S$ is expressed by the following Equation (7).

[Equation 7]

$$S_s = \frac{\pi}{2}\left(R - \frac{RM}{\sqrt{\frac{R^2}{4}+H^2}}\right)\left(\sqrt{\frac{R^2}{4}+H^2} - M\right)$$

(7)

Since the lost periodontal membrane area $S_L$=total periodontal membrane area S—remaining periodontal membrane area $S_S$, the lost periodontal membrane area $S_L$ is represented by the following Equation (8).

[Equation 8]

$$S_L = \frac{\pi}{2}\left\{R\sqrt{\frac{R^2}{4}+H^2} - \left(R - \frac{RM}{\sqrt{\frac{R^2}{4}+H^2}}\right)\left(\sqrt{\frac{R^2}{4}+H^2} - M\right)\right\}$$

(8)

4) The values of the root length H and the diameter R shown in Table 3, which differ according to the type of the tooth, are entered into the above Equations (5), (7) and (8). Further, the values of the sample attachment level classified by the type of the tooth at the time of loss of each tooth, which are shown in Table 1, are entered into Equations (5), (7) and (8) to calculate the total periodontal membrane area S, the remaining periodontal membrane area $S_S$, and the lost periodontal membrane area $S_L$ of the root of each tooth type at the time of loss of the tooth. The results are shown in Table 4.

If the total periodontal membrane area S, the remaining periodontal membrane area $S_S$, and the lost periodontal membrane area $S_L$ given by the aforementioned Equations (5), (7) and (8) are utilized as such, they are insufficient as indices representing the severity of progression of periodontal disease, as have been discussed earlier. In the present embodiment, therefore, influences ascribed to differences in bite force among the various teeth are investigated, and the results are reflected in the creation of a predetermined index. That is, we speculated that an index accurately reflecting the severity of progression of periodontitis for each tooth type might be obtained by correcting the remaining periodontal membrane area $S_S$ and the lost periodontal membrane area $S_L$ with bite force. Based on this speculation, the following investigation was conducted.

Complicated bite force is presumed to act on each tooth as external force, and is corrected with the following two factors which can become predominant factors:

1) If the cusp of each tooth is assumed to be the point of action in leverage, the condyle of the temporomandibular joint is considered to be the fulcrum of the lever. Thus, bite force is corrected with the ratio between the distance from the cusp of the mandibular first tooth, as a reference, to the condyle of the temporomandibular joint and the distance from the cusp of the tooth of each type to the condyle of the temporomandibular joint. That is, the molar tooth is nearer to the condyle than is the anterior tooth, and is thus considered to undergo stronger bite force.

2) It is assumed that the larger the length from the cusp subjected to bite force to the apex of the root, the more easily the bite force works as traumatic force under the principle of the lever. Thus, the distance from the site, where the maxillary and mandibular teeth clinically make occlusal contact, to the farthest root apex is used as the length of the tooth. Then, bite force is corrected by the ratio between the length of the mandibular first tooth, as a reference, and the length of the tooth of each type.

In consideration of 1) and 2) above, a bite force coefficient B representing the relationship between the bite forces on the respective teeth is worked out. The bite force coefficient B is calculated in connection with each tooth based on the ratio between the distance T from the cusp of each tooth to the condyle of the temporomandibular joint, and the distance A from a specific reference tooth providing a reference position to the above condyle; and the ratio between the tooth length P of the reference tooth and the length Q of each tooth mentioned above, these data being preliminarily given as anatomical data. In calculating the bite force coefficient B, the cusp of each tooth mentioned above is taken as the point of action of a lever, and the above condyle is taken as the fulcrum of the lever.

That is, the bite force coefficient B is given by the following Equation (9):

[Equation 9]

$$\text{Bite force coefficient } B = \frac{TP}{AQ} \quad (9)$$

Here, the following hypothesis is set up: The lost periodontal membrane area $S_L$ at the time of loss of each tooth based on the sample attachment level M is different among the respective tooth types, as shown in the aforementioned Table 4. If the above parameter $S_L$ is rendered comparable among the different tooth types by undergoing corrections taking bite force into consideration, it can be said that "the cause of periodontal membrane loss is bite force".

Thus, the corrected values were compared. Concretely, the lost periodontal membrane area $S_L$ shown in Table 4 was multiplied by the bite force coefficient B shown in Table 5 to obtain the bite force-corrected value ($S_L$·B) of the periodontal membrane area $S_L$ at the time of loss of the tooth of each tooth type. The resulting values are shown in Table 6.

TABLE 5

Bite force coefficient (B) for each tooth type

| B | 0.888 | 0.895 | 0.688 | 0.764 | 0.573 | 0.490 |
|---|---|---|---|---|---|---|
| Q | 19.0 | 20.4 | 22.2 | 19.7 | 22.7 | 23.3 |
| T | 88 | 84 | 77 | 66 | 57 | 48 |
| Tooth type | 1 | 2 | 3 | 45 | 6 | 7 |
| T | A 88 | 84 | 79 | 74 | 60 | 54 |
| Q | P 19.6 | 20.8 | 21.0 | 20.9 | 22.3 | 17.7 |
| B | 1.0 | 0.921 | 0.754 | 0.807 | 0.613 | 0.696 |

T: Distance from bite force functioning site for each tooth type to condyle of temporomandibular joint
Q: Distance from cusp tip of each tooth type to root apex
B: Bite force coefficient TP/AQ

TABLE 6

Lost periodontal membrane area ($S_L$) for each tooth type and bite force-corrected values of $S_L$ ($S_L$B)

| 94.8 | 121.3 | 118.0 | 85.2 | 79.2 | 108.7 | $S_L$B | 97.7 | 89.3 | 104.0 | 101.3 | 119.0 | 97.1 |
| 193.4 | 211.7 | 154.4 | 123.9 | 88.5 | 122.4 | $S_L$ | 110.0 | 99.8 | 151.1 | 132.6 | 207.6 | 198.1 |
| 7 | 6 | 54 | 3 | 2 | 1 | type of tooth | 1 | 2 | 3 | 45 | 6 | 7 |
| 122.3 | 187.5 | 98.6 | 119.7 | 93.0 | 87.6 | $S_L$ | 85.7 | 94.6 | 107.0 | 88.5 | 208.0 | 130.0 |
| 85.1 | 114.9 | 79.6 | 90.3 | 85.7 | 87.6 | $S_L$B | 85.7 | 87.1 | 80.7 | 71.4 | 127.5 | 90.5 |

Next, the lost periodontal membrane area $S_L$ for each tooth type and the lost periodontal membrane area $S_L$·B corrected with the bite force coefficient B taken into consideration were compared among the respective tooth types. The results are as follows:

1) Lost periodontal membrane area $S_L$ a) Differences according to the type of tooth were noted (P=0.0000013, two-way factorial ANOVA without replication).

b) Differences were noted between the maxillary teeth and the mandibular teeth (P=0.0046, two-way factorial ANOVA without replication).

c) No differences were found between the right side and the left side (paired t-test).

d) Differences due to the type of tooth were found, except the upper and lower right and left sixth teeth (P=0.0014, two-way factorial ANOVA without replication), but no differences were found between the upper jaw and the lower jaw and between the left side and the right side (two-way factorial ANOVA without replication and paired t-test).

2) $S_L$·B corrected with bite force coefficient B taken into consideration a) Differences according to the type of tooth were noted (P=0.0025, two-way factorial ANOVA without replication).

b) No differences were found between the upper jaw and the lower jaw and between the left side and the right side (differences between the left side and the right side were not significant in two-way factorial ANOVA without replication or in paired t-test).

c) Differences due to the type of tooth were not found, except the upper and lower right and left sixth teeth. Nor were differences found between the upper jaw and the lower jaw and between the left side and the right side (two-way factorial ANOVA without replication and paired t-test).

Based on 1) and 2) above in view of the above findings, it can be concluded that "the cause of periodontal membrane loss is bite force", except for the upper and lower sixth teeth.

In the light of the fact that "the cause of periodontal membrane loss is bite force" as described above, a graph was prepared, with the bite force coefficient B being set for the horizontal axis and the lost periodontal membrane area $S_L$ being set for the vertical axis, in order to investigate the relationship between the bite force coefficient B and an at-time-of-loss lost periodontal membrane area $S_{LBO}$ at the time of loss of tooth based on the sample attachment level M.

Figure 5:
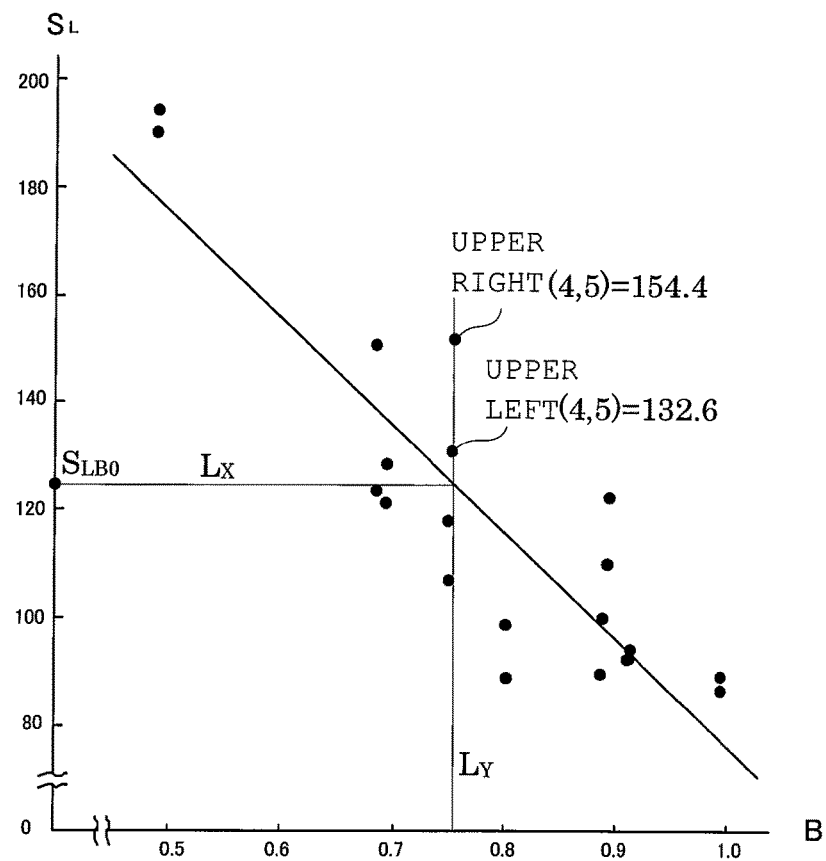
FIG. 5 is a graph showing the relationship between the bite force coefficient and the at-time-of-loss lost periodontal membrane area which is a lost periodontal membrane area at the time of loss of a tooth.

Next, the values of the bite force coefficient B and the lost periodontal membrane area $S_L$ in four samples per tooth type were plotted in the graph shown in FIG. 5, because "no differences were found between the upper jaw and the lower jaw and between the left side and the right side", based on the results of statistical processing of the values of the lost periodontal membrane area $S_L$ and the bite force coefficient B.

The relationship between the bite force coefficient (B) and the lost periodontal membrane area ($S_L$) in this case is shown in Table 7.

TABLE 7

"Bite force-lost periodontal membrane straight line" data

| | | | | | | | | | | |
|---|---|---|---|---|---|---|---|---|---|---|
| 193.4 | 154.4 | 123.9 | 88.5 | 122.4 | $S_L$ | 110.0 | 99.8 | 151.1 | 132.6 | 198.1 |
| 0.490 | 0.764 | 0.688 | 0.895 | 0.888 | B | 0.888 | 0.895 | 0.688 | 0.764 | 0.490 |
| 7 | 54 | 3 | 2 | 1 | type of tooth | 1 | 2 | 3 | 45 | 7 |
| 0.696 | 0.807 | 0.754 | 0.921 | 1.0 | B | 1.0 | 0.921 | 0.754 | 0.807 | 0.696 |
| 122.3 | 98.6 | 119.7 | 93.0 | 87.6 | $S_L$ | 85.7 | 94.6 | 107.0 | 88.5 | 130.0 |

$S_L$: Lost periodontal membrane area
B: Bite force coefficient TP/AQ
T: Distance from bite force functioning site for each tooth type to condyle of temporomandibular joint
P: Distance from incisal edge of lower first anterior tooth to root apex
A: Distance from incisal edge of lower first anterior tooth to condyle of temporomandibular joint
Q: Distance from cusp tip of each tooth type to root apex A total of 20 samples, excluding the sixth teeth, were statistically processed, showing that a very highly linear correlation was present between the bite force coefficient B and the lost periodontal membrane area $S_L$ at the time of loss of tooth (correlation coefficient=−0.8826, adjusted R-squared=0.7667). That is, the following linear relation $$S_L = -203.9B + 281.2 \quad (10)$$

holds between the bite force coefficient B and the lost periodontal membrane area $S_L$ at the time of loss of tooth.

The straight line represented by the above Equation (10), namely, "bite force-lost periodontal membrane straight line", indicates that the bite force coefficient B and the lost periodontal membrane area $S_L$ are in parallel correspondence. By finding such "bite force-lost periodontal membrane straight line", therefore, a concrete example can be replaced by a generality. That is, the bite force coefficient B is an anatomical value, and a preliminarily given constant. On the other hand, the upper jaw and the lower jaw differ in the points of occlusion, so that their distances from the occlusion point to the condyle of the temporomandibular joint and their tooth lengths are also different. Moreover, because of their anatomical differences, they are different between the Oriental people and the Western people. Thus, the bite force-lost periodontal membrane straight line can be said to be a universal equation showing the relation between the bite force coefficient B and the lost periodontal membrane area $S_L$ at the time of loss of tooth.

Hence, if the bite force coefficient B of a specific tooth is substituted into the above Equation (10), one lost periodontal membrane area $S_L$ is specified. This lost periodontal membrane area $S_L$ is a value representing the at-time-of-loss lost periodontal membrane area $S_{LBO}$ at the time of loss (extraction) of tooth, which takes into consideration the bite force coefficient B preliminarily given as an anatomical constant. The at-time-of-loss lost periodontal membrane area $S_{LBO}$ is uniquely determined if the bite force coefficient B as the anatomical constant is found.

That is, as shown in FIG. 5, the at-time-of-loss lost periodontal membrane area $S_{LBO}$ is obtained by extending a straight line $L_Y$ in the vertical axis direction from a specific bite force coefficient B to bring the straight line $L_Y$ into contact with the bite force-lost periodontal membrane straight line, extending a straight line $L_X$ in the horizontal axis direction from the point of contact to bring the straight line $L_X$ into contact with the vertical axis, and taking the point of contact with the vertical axis as the value of the lost periodontal membrane area $S_L$.

The same treatment is performed for each bite force coefficient B, whereby the at-time-of-loss lost periodontal membrane area $S_{LBO}$ at the time of loss of tooth taking into consideration the bite force coefficient B of each tooth which gives each bite force coefficient B can be obtained.

Here, the remaining periodontal membrane area $S_S$ is given as $S_S$=total periodontal membrane area S—lost periodontal membrane area $S_L$. Thus, the at-time-of-loss remaining periodontal membrane area $S_{SBO}$, which is the remaining periodontal membrane area $S_S$ at the time of loss of a specific tooth providing the sample attachment level M, is given as $S_{SBO}$=total periodontal membrane area S—at-time-of-loss lost periodontal membrane area $S_{LBO}$.

Against the above-mentioned background, the periodontal index BPI (Periodontal Index Modified with Bite Force), which reflects the progression of periodontitis more appropriately, can be defined as the ratio of the remaining periodontal membrane area $S_{SB}$ taking the bite force coefficient B into consideration to the total periodontal membrane area S. That is, the periodontal index BPI in the present embodiment is defined as BPI=($S_{SB}$/S)×100(%).

To use the periodontal index BPI as an index to representing the severity of progression of periodontitis, the remaining periodontal membrane area $S_S$ of a tooth, if it is to be used as a variable, needs to be modified into the remaining periodontal membrane area $S_{SB}$ taking the bite force coefficient B into consideration. This is achievable by the following procedure, which will be explained based on FIG. 6.

1) First, the remaining periodontal membrane area $S_S$ is set for the horizontal axis and the periodontal index BPI is set for the vertical axis. In this case, a straight line, connecting two points representing 100 which is the periodontal index BPI when all the periodontal membrane remains, and 0 which is the periodontal index BPI when all the periodontal membrane is lost, is drawn.

2) Then, the value of the periodontal index BPI at the time of loss of tooth which is given as the value based on the at-time-of-loss remaining periodontal membrane $S_{SBO}$ at the time of loss of tooth (i.e., point $P_{50}$=50 in FIG. 6) is plotted. The above-mentioned straight line is moved in parallel so as to become a straight line passing through the plotted point $P_{50}$.

3) Further, a periodontal index curve is prepared as a smooth curve which passes through the two points representing the periodontal indices BPI of 0 and 100, and contacts the parallel-moved straight line only at the plotted point.

Figure 6:
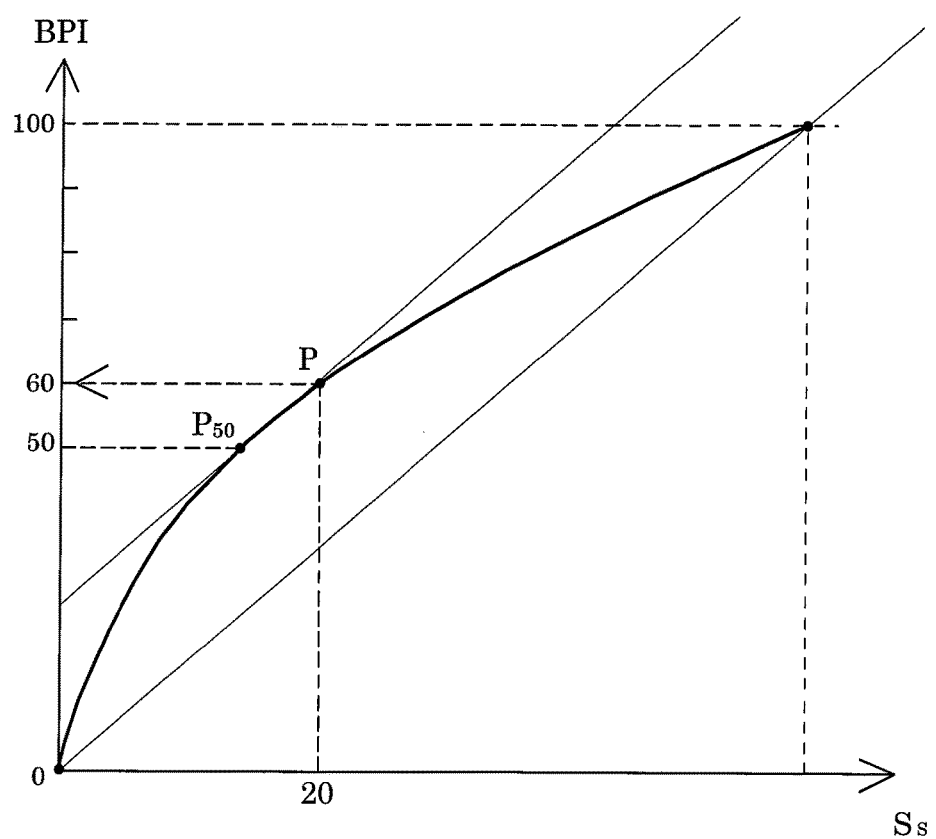
FIG. 6 is an explanation drawing of a method for preparing a periodontal index curve showing the relationship between the remaining periodontal membrane area taking bite force into consideration and the periodontal index BPI.

4) A point P on the periodontal index curve corresponding to a specific remaining periodontal membrane area $S_S$, such as the remaining periodontal membrane area $S_S$ of the tooth as the object of medical examination, is taken as a periodontal index BPI corresponding to the specific remaining periodontal membrane area $S_S$. In FIG. 6, BPI=60.

The periodontal index BPI defined in the present embodiment is given as the point on the periodontal index curve corresponding to any remaining periodontal membrane area $S_S$. As noted here, simply by specifying the remaining periodontal membrane area $S_S$, a desired periodontal index BPI taking bite force into consideration can be obtained with the use of the periodontal index curve.

Such a periodontal index BPI is an objective index appropriately reflecting the severity of progression of periodontitis. This index, as an index presenting tooth extraction criteria objectively, can serve as an absolute index to the health of tooth conformed to the clinical status of periodontal disease more accurately.

The periodontal index BPI in the present embodiment is defined, with concepts such as the pseudo-root and the bite force coefficient B being introduced. Explanations will be offered here for anatomical data for deriving the pseudo-root and the bite force coefficient B. In the present embodiment, the races in the world with different skeletons were broadly classified into two categories, the Oriental people and the Western People. For the Oriental people, data from Yasuhiko Kamijou, "Anatomy of Permanent Teeth in the Japanese (literally)", published by Anatome Co., Ltd., indicating periodontitis and bite force, were used as representative data.

For the Western people, on the other hand, data from the following two documents were used as representative data:
    Root width, root length: Woelfel's Dental Anatomy
        Rickne c. Seheid
        Gadriela Weiss
        Wolters Kluwer
    Temporomandibular joint: Head and Neck Anatomy for Dental Medicine
        Edited by Eric W. Baker
        Thieme From the respective documents above, the following data were compiled:
    R: Root (CEJ portion) diameter (mm)
    H: Root length (mm)
    Q: Distance from cusp tip to root apex (length of tooth)
    T: Distance from bite force functioning site to condyle of temporomandibular joint
    P: Distance from incisal edge of lower first anterior tooth to root apex
    A: Distance from incisal edge of lower first anterior tooth to condyle of temporomandibular joint In connection with the Oriental people and the Western people, the anatomical data are shown in Table 8, the total periodontal membrane areas and the bite force coefficients are shown in Table 9, and the at-time-of-loss remaining periodontal membrane area $S_{SBO}$ and the at-time-of-loss lost periodontal membrane area $S_{LBO}$ at the time of loss of each tooth are shown in Table 10.

TABLE 8

Anatomical data in Oriental and Western people

Oriental people

| | | | | | | | |
|---|---|---|---|---|---|---|---|
| R | 6.5 | 5.2 | 7.0 | B 4.6<br>P 4.6 | B 4.2<br>P 4.2 | BM 4.2<br>BD 4.2<br>P 6.0 | BM 3.7<br>PD 3.7<br>P 4.8 |
| H | 11.8 | 12.1 | 15.6 | B 12.3<br>P 12.3 | B 12.7<br>P 12.7 | BM 11.5<br>BD 11.5<br>P 11.1 | BM 11.6<br>PD 11.6<br>P 12.3 |
| Q | 19.0 | 20.4 | 22.2 | 19.3 | 20.0 | 22.7 | 22.3 |

TABLE 8-continued

Anatomical data in Oriental and Western people

| | | | | | | | |
|---|---|---|---|---|---|---|---|
| T | 88 | 84 | 77 | 68 | 64 | 57 | 48 |
| | 1 | 2 | 3 | 4 | 5 | 6 | 7 |
| A | 86 | | | | | | |
| P | 19.6 | | | | | | |
| T | 86 | 84 | 79 | 77 | 71 | 60 | 54 |
| Q | 19.6 | 20.8 | 21.0 | 21.2 | 20.6 | 22.3 | 17.7 |
| H | 11.2 | 11.5 | 14.0 | 13.3 | 13.1 | M 12.2<br>D 12.8 | M 11.9<br>D 12.2 |
| R | 4.9 | 5.2 | 6.0 | 5.9 | 6.3 | M 6.8<br>D 6.8 | M 5.8<br>D 5.8 |

Western people

| | | | | | | | |
|---|---|---|---|---|---|---|---|
| R | 6.4 | 5.3 | 6.6 | B 4.5<br>P 4.5 | B 4.4<br>P 4.4 | BM 4.7<br>BD 4.7<br>P 6.7 | BM 4.6<br>BD 4.6<br>P 6.5 |
| H | 13.0 | 13.4 | 16.5 | B 13.4<br>P 13.4 | B 14.0<br>P 14.0 | BM 12.9<br>BD 12.2<br>P 13.7 | BM 12.9<br>BD 12.1<br>P 13.5 |
| Q | 23.6 | 22.5 | 26.3 | 21.5 | 21.2 | 20.1 | 20.0 |
| T | 96 | 93 | 89 | 84 | 78 | 70 | 61 |
| | 1 | 2 | 3 | 4 | 5 | 6 | 7 |
| A | 96 | | | | | | |
| P | 20.8 | | | | | | |
| T | 96 | 93 | 91 | 87 | 80 | 72 | 63 |
| Q | 20.8 | 22.1 | 25.9 | 22.4 | 22.1 | 20.9 | 20.6 |
| H | 12.6 | 13.5 | 15.9 | 14.4 | 14.7 | M 14.4<br>D 13.0 | M 13.9<br>D 13.0 |
| R | 4.5 | 4.8 | 6.4 | 5.9 | 6.2 | M 6.8<br>D 6.8 | M 6.7<br>D 6.7 |

TABLE 9

Total periodontal membrane areas (S) and bite force coefficients (B) in Oriental people and Western people Oriental people

| | | | | | | | |
|---|---|---|---|---|---|---|---|
| B | 0.888 | 0.895 | 0.688 | 0.803 | 0.730 | 0.573 | 0.490 |
| S | 125.0 | 101.1 | 175.8 | 180.8<br>B 90.42 | 169.8<br>B 84.92 | 262.6<br>BM 77.12<br><br>BD 77.12 | 231.0<br>BM 68.27<br>BD 68.27 |
| | | | | P 90.42 | P 84.92 | | |
| | | | | | | P 108.37 | P 94.49 |
| | 1 | 2 | 3 | 4 | 5 | 6<br>M 135.28<br>D 141.46 | 7<br>M 111.59<br>D 114.25 |
| S | 88.2 | 96.3 | 134.9 | 126.3 | 133.3 | 276.7 | 225.8 |
| B | 1.0 | 0.921 | 0.754 | 0.828 | 0.786 | 0.613 | 0.696 |

Western people

| | | | | | | | |
|---|---|---|---|---|---|---|---|
| B | 0.883 | 0.897 | 0.734 | 0.848 | 0.798 | 0.756 | 0.662 |
| S | 134.6 | 113.7 | 174.5 | 192.1<br>B 96.04<br><br>P 96.04 | 195.9<br>B 97.95<br><br>P 97.95 | 337.0<br>BM 96.80<br><br>BD 91.73<br>P 148.43 | 325.5<br>BM 94.68<br>BD 89.00<br>P 141.78 |
| | 1 | 2 | 3 | 4 | 5 | 6<br>M 158.04<br>D 143.53 | 7<br>M 150.48<br>D 141.29 |
| S | 90.5 | 103.4 | 163.1 | 136.2 | 146.3 | 301.6 | 291.8 |
| B | 1.0 | 0.913 | 0.762 | 0.843 | 0.786 | 0.748 | 0.664 |

B: Buccal root
P: Palatal root
BM: Buccomesial root
BD: Buccodistal root
M: Mesialroot
D: Distalroot

TABLE 10

At-time-of-loss $S_L$ and at-time-of-loss $S_S$ in Oriental people and Western people Oriental people

| | | | | | | | |
|---|---|---|---|---|---|---|---|
| At-time-of-loss $S_S$ | 24.8 | 2.38 | 34.9 | 63.4 | 37.5 | 98.2 | 49.7 |
| At-time-of-loss $S_L$ | 100.1 | 98.7 | 140.9 | 117.5 | 132.4 | 164.4 | 181.3 |
| | 1 | 2 | 3 | 4 | 5 | 6 | 7 |
| At-time-of-loss $S_L$ | 77.3 | 93.4 | 127.5 | 112.4 | 120.9 | 156.2 | 139.3 |
| At-time-of-loss $S_S$ | 10.9 | 2.89 | 7.48 | 13.9 | 12.4 | 120.5 | 86.6 |

Western people

| | | | | | | | |
|---|---|---|---|---|---|---|---|
| At-time-of-loss $S_S$ | 33.4 | 15.4 | 42.9 | 83.8 | 77.4 | 209.9 | 179.2 |
| At-time-of-loss $S_L$ | 101.2 | 98.3 | 131.5 | 108.3 | 118.5 | 127.1 | 146.2 |
| | 1 | 2 | 3 | 4 | 5 | 6 | 7 |
| At-time-of-loss $S_L$ | 77.3 | 95.0 | 125.8 | 109.3 | 120.9 | 128.7 | 145.8 |
| At-time-of-loss $S_S$ | 13.2 | 8.34 | 37.2 | 26.9 | 25.4 | 172.9 | 146.0 |

Figure 7:
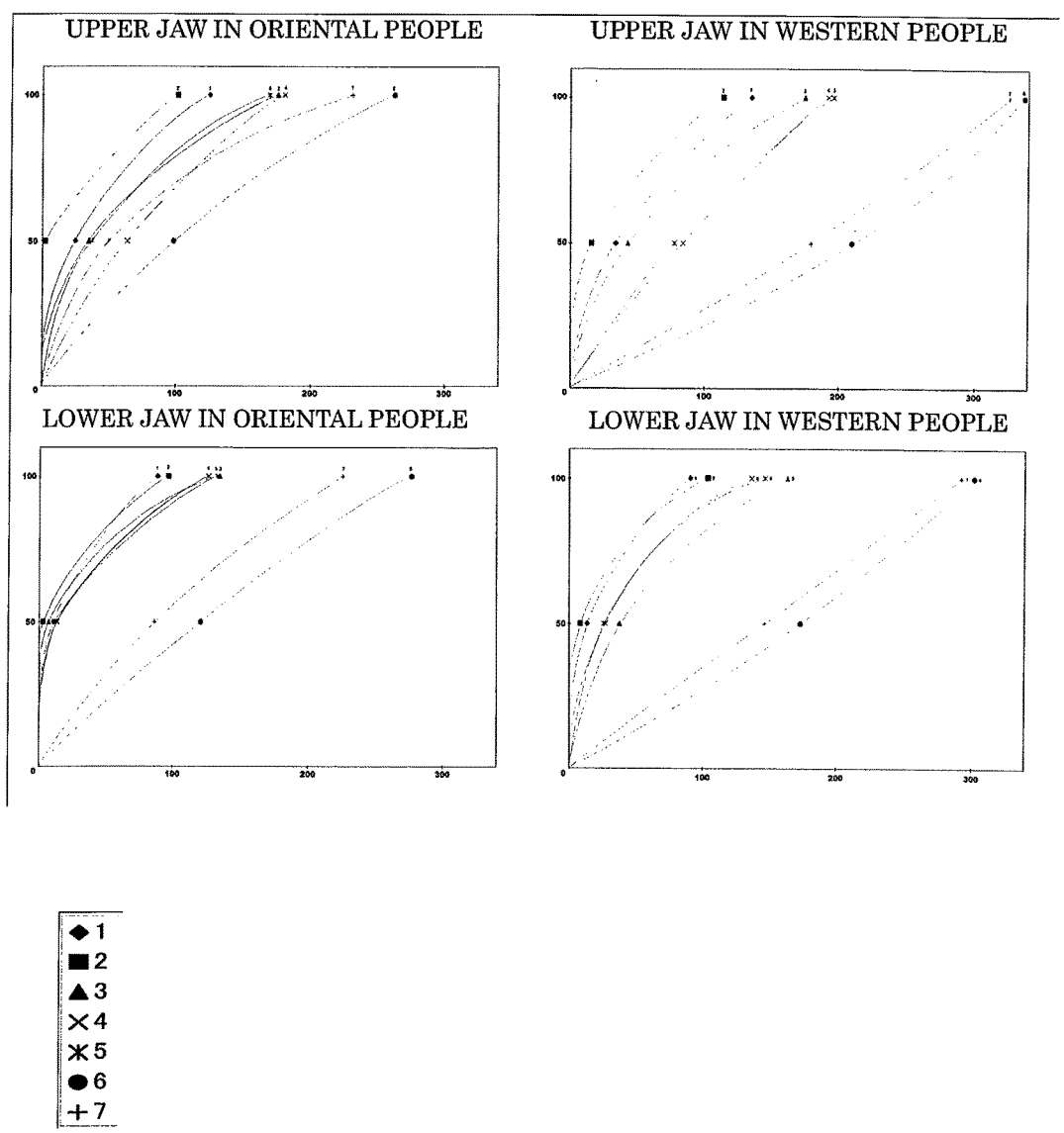
FIG. 7 is graphs showing the periodontal index curves, different according to race and tooth type, in connection with the upper jaw and the lower jaw.

FIG. 7 shows BPI curves classified by the type of tooth in the Oriental people and the Western people which were prepared using the above anatomical data. By specifying the remaining periodontal membrane area $S_S$ of the tooth as the object of examination, the corresponding periodontal index BPI classified by race can be found easily by use of the BPI curve classified by tooth type.

If the BPI curves by tooth type shown in FIG. 7 are used, the periodontal index BPI of the desired tooth can be obtained arbitrarily, and can be used for diagnosing periodontitis.

In diagnosing periodontitis, the attachment level of the tooth which is the object of diagnosis is measured to determine the measured attachment level M1. Such a measurement can be made preferably using a pocket probe, for example. The measurement is performed at six locations, i.e., the buccal root, the palatal root, the buccomesial root, the buccodistal root, the mesial root, and the distal root of the tooth, and the largest value is adopted as the measured attachment level M1.

Then, the remaining periodontal membrane area $S_S$ is found based on the measured attachment level M1 by a method as described earlier. Of the BPI curves classified by tooth type in FIG. 7, the BPI curve w corresponding to the tooth as the object of diagnosis is selected, the point corresponding to the remaining periodontal membrane area $S_S$ is specified on its horizontal axis, the point on the BPI curve corresponding to this point is found, and the periodontal index BPI on the vertical axis corresponding to the found point is read.

Based on the value of the periodontal index BPI thus obtained, the severity of progression of periodontitis is diagnosed. The higher this value, the healthier the tooth is. Thus, it is possible to draw attention to the progression of periodontitis, for example, by setting BPI of 40 to 60 in a precaution region, BPI of less than 40 in a dangerous region, and BPI of more than 60 in a safety region.

In the periodontal index creation method according to the present embodiment, there are provided the three points, i.e., the one point giving the at-time-of-loss periodontal index BPI taking bite force into consideration, which is obtained based on FIG. 5 and, added thereto, the point where the periodontal index BPI is zero (all the periodontal membrane is lost, and the remaining periodontal membrane area $S_S$ is zero), and the point where the periodontal index BPI is 100 (all the periodontal membrane remains, and the remaining periodontal membrane area $S_S$ is equal to the total periodontal membrane area). Thus, a single periodontal index curve is uniquely established by the processings mentioned above. However, no particular restrictions are imposed on the method for preparation of the periodontal index curve, as long as it is a method utilizing the at-time-of-loss periodontal index BPI taking bite force into consideration which is obtained based on FIG. 5.

There is a case where the periodontal index creation step is not necessarily needed. The reasons are as follows: If the at-time-of-loss periodontal index BPI taking bite force into consideration, which is obtained based on FIG. 5, is found, this parameter BPI may be usable, alone, as objective criteria for tooth extraction. If only the at-time-of-loss periodontal index BPI is determined, moreover, the periodontal index BPI, which is the ratio between the remaining periodontal membrane area $S_{SB}$ taking bite force into consideration and the total periodontal membrane area S, is considered to be obtainable using the at-time-of-loss periodontal index BPI by various methods.

<Periodontal Index Creation Apparatus and Periodontitis Diagnosis Apparatus>

Figure 8:
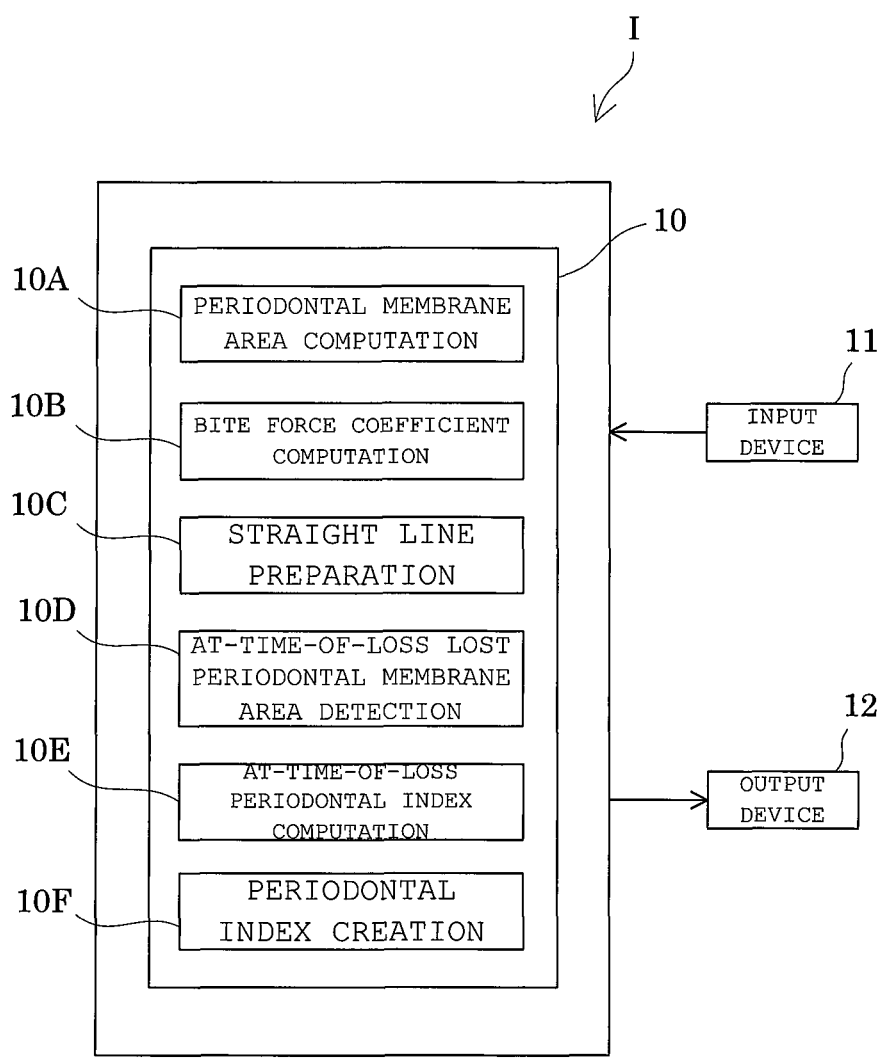
FIG. 8 is a block diagram showing a periodontal index creation apparatus according to an embodiment of the present invention.
Figure 9:
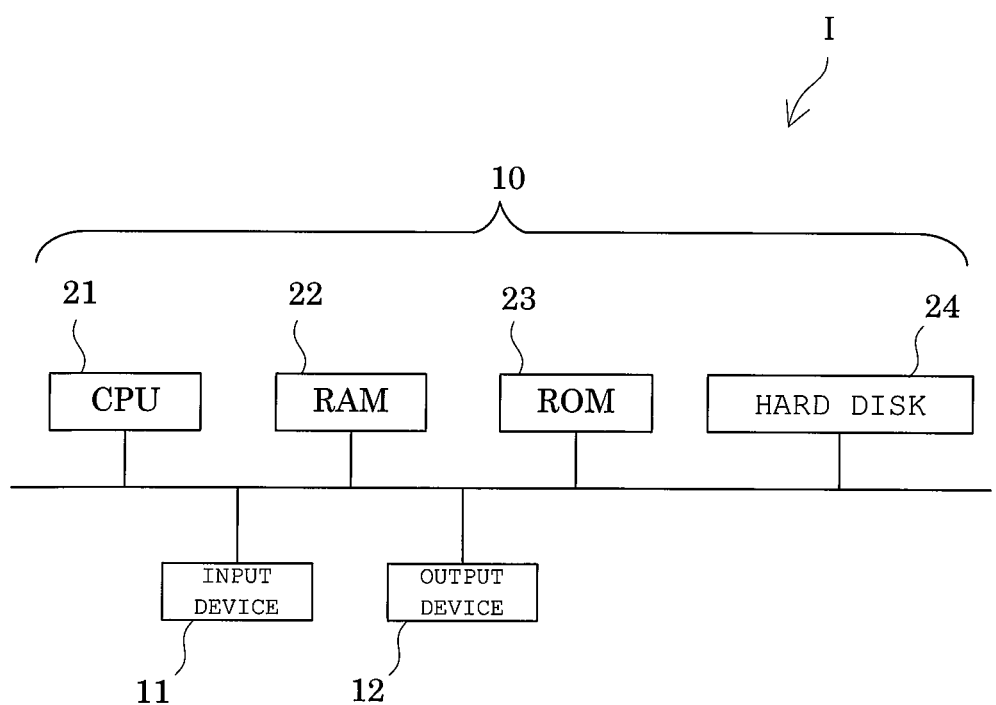
FIG. 9 is a block diagram showing the hardware configuration of a computation unit of the apparatus illustrated in FIG. 8.

FIG. 8 is a block diagram showing a periodontal index creation apparatus according to the embodiment of the present invention. FIG. 9 is a block diagram showing the hardware configuration of a computation unit of this apparatus. As shown in FIG. 8, a periodontal index creation apparatus 1 is composed of an input device 11, a computation unit 10 for receiving input of predetermined data via the input device 11 and performing predetermined information processings, and an output device 12 for outputting the results of the processings performed by the computation unit 10.

The input device 11 supplies data necessary for computation, such as data representing the sample attachment level M which is basic data for creating the periodontal index BPI, and data representing the measured attachment level M1 measured in connection with the target tooth for making a diagnosis of periodontitis.

The computation unit 10 includes a periodontal membrane area computing means 10A, a bite force coefficient computing means 10B, a straight line preparing means 10C, an at-time-of-loss lost periodontal membrane area detecting means 10D, an at-time-of-loss periodontal index computing means 10E, and a periodontal index creating means 10F.

The periodontal membrane area computing means 10A calculates the lost periodontal membrane area $S_S$ of each tooth based on the total periodontal membrane area (S) of each tooth and the sample attachment level M of each tooth extracted. Simultaneously, the periodontal membrane area computing means 10A also calculates the remaining periodontal membrane area $S_S$ based on the measured attachment level M1 of a specific tooth as the object of diagnosis.

The bite force coefficient computing means 10B calculates the bite force coefficient B in connection with each tooth based on the ratio between the distance T from the cusp of each tooth to the condyle of the temporomandibular joint, and the distance A from a specific reference tooth providing a reference position to the above condyle; and the ratio between the tooth length P of the preliminarily given reference tooth and the length Q of each tooth, these parameters T, A, P and Q being preliminarily given as anatomical data, such that bite force acts, with the cusp of each tooth serving as the point of action of a lever, and the condyle serving as the fulcrum of the lever.

The straight line preparing means 10C prepares a bite force-lost periodontal membrane straight line which is a linear equation ($S_L = \alpha \cdot B + \beta$; $\alpha$ and $\beta$ are constants) showing the relation between the bite force coefficient B different according to the type of tooth alone and the lost periodontal membrane area $S_L$ with the aid of the fact that when the relation between the bite force coefficient B and the lost periodontal membrane area $S_L$ is statistically processed for each tooth type, a linear relation is present between the values of both parameters.

The at-time-of-loss lost periodontal membrane area detecting means 10D calculates the at-time-of-loss lost periodontal membrane area $S_{LBO}$ which is the lost periodontal membrane area of each tooth, at the time of loss, corrected in consideration of the bite force coefficient B, based on the bite force-lost periodontal membrane straight line obtained by the straight line preparing means 10C.

The at-time-of-loss periodontal index computing means 10E calculates the parameter (at-time-of-loss remaining periodontal membrane area ($S_{SBO}$)/total periodontal membrane area (S))×100(%) as the periodontal index BPI at the time of loss of each tooth, based on an at-time-of-loss remaining periodontal membrane area obtained by subtracting the at-time-of-loss lost periodontal membrane area from the total periodontal membrane area.

The periodontal index creating means 10F creates a periodontal index BPI which is the proportion of the remaining periodontal membrane area $S_S$ taking the bite force coefficient of each tooth into consideration to the total periodontal membrane area S, the index being represented by a periodontal index curve passing through three points representing a value of 100 being a periodontal index (BPI) when all of the periodontal membrane remains, a value of 0 being a periodontal index (BPI) when all of the periodontal membrane is lost, and a value being a periodontal index at the time of loss of each tooth (i.e., $S_{SBO}$/S) as the at-time-of-loss periodontal index. At the same time, the periodontal index creating means 10F obtains the periodontal index BPI corresponding to the remaining periodontal membrane area $S_S$ calculated based on the measured attachment level M1 of a specific tooth as the object of diagnosis, by reference to the periodontal index curve, thereby creating the periodontal index BPI of the specific tooth as the object of diagnosis.

The output device 12 receives input of data representing the periodontal index BPI created by the periodontal index creating means 10F, and visualizes the contents of the data by printing, displaying or the like.

The computation unit 10 shown in FIG. 9 is equipped with storage means such as CPU 21, RAM 22, ROM 23, and a hard disk 24. The input device 11 such as a keyboard or a recording medium reader, and the output device 12 such as a display or a printer are connected to the computation unit 10.

According to the present embodiment, the periodontal index BPI taking bite force into consideration can be obtained automatically with ease, simply by inputting sampling data on the sample attachment level M into the computation unit 10. As a result, an absolute index to the health of a tooth conformed to the clinical status of periodontal disease with higher accuracy can be provided easily.

Simply by inputting data on the measured attachment level M1 of the specific tooth as the object of diagnosis, moreover, a periodontal index BPI taking bite force, different according to the type of tooth, into consideration can be determined easily and automatically. Thus, unerring and objective tooth extraction criteria for periodontitis treatment can be easily obtained. Hence, appropriate treatment of periodontitis can be conducted easily and promptly.

In the periodontal index creation apparatus according to the present embodiment, there may be a case where the periodontal index creating means 10F is not necessarily needed, for the same reasons as those mentioned in connection with the periodontal index creation method.

<Periodontal Index Creation Program and Periodontitis Diagnosis Program>

The present embodiment is a program for allowing the periodontal index creation apparatus or the periodontitis diagnosis apparatus to execute the processings of the periodontal membrane area computation step, the bite force coefficient computation step, the lost periodontal membrane area detection step, the at-time-of-loss periodontal index computation step, and the periodontal index creation step in the periodontal index creation method described in the aforementioned embodiment.

According to the present embodiment, the periodontal index creation apparatus shown in FIG. 8 can be allowed to satisfactorily execute the processings of the predetermined steps in the periodontal index creation method according to the aforementioned embodiment.

Another embodiment is a program which comprises: allowing the periodontitis diagnosis apparatus, shown in FIG. 8, to perform processings for calculating the remaining periodontal membrane area $S_S$ of the tooth as the object of diagnosis based on the measured attachment level M1 in the periodontitis diagnosis method of the above-mentioned embodiment, and creating the periodontal index BPI of the specific tooth, as the object of diagnosis, corresponding to the remaining periodontal membrane area $S_S$ by the periodontal index creation step.

According to the present embodiment, the predetermined periodontal index can be generated automatically to contribute to the easy and prompt treatment of periodontitis.

<Recording Medium>

The above periodontal index creation program and the periodontitis diagnosis program can be recorded on a recording medium such as DVD. Such a recording medium enables distribution or the like of the program according to the present invention to be carried out satisfactorily. As a result, if there is hardware such as a personal computer, the hardware having the programs installed thereon via the recording medium can easily function anywhere as a periodontal index creation apparatus.

The present invention can be utilized suitably in dental care fields, particularly, in industrial fields for providing objective tooth extraction criteria when performing treatment of periodontal disease.

The invention claimed is:

1. A method for diagnosing periodontitis and tooth extraction for a patient, comprising:

obtaining a plurality of extracted teeth which have been judged to be unconservable so as to obtain extracted unconservable teeth;

measuring a sample attachment level for a plurality of samples taken from each tooth of the plurality of extracted unconservable teeth to determine a greatest sample attachment level for each tooth of the plurality of extracted unconservable teeth, the sample attachment level being a dimension ranging from a cementoenamel junction of the respective tooth, for teeth not including a veneer crown, or from a crown margin of the respective tooth, for teeth having a veneer crown, to a lowermost site of a submarginal dental calculus deposited portion of the respective tooth;

calculating a lost periodontal membrane area of each tooth of the plurality of extracted unconservable teeth based on a total periodontal membrane area of the respective tooth and the greatest sample attachment level for the respective tooth;

finding a bite force coefficient for each tooth of the plurality of extracted unconservable teeth, the bite force coefficient for each tooth being calculated based on a ratio between (1) a measured distance from a cusp of the respective tooth to a condyle of a temporomandibular joint of the respective tooth and (2) an expected distance between the cusp and the condyle for the respective tooth, and on a ratio between an expected length of the respective tooth and a measured length of the respective tooth;

preparing a chart comprising a bite force-lost periodontal membrane straight line, the bite force-lost periodontal membrane straight line being based on a linear equation showing a relationship between the bite force coefficient and the lost periodontal membrane area for each tooth of the plurality of extracted unconservable teeth, the straight line being calculated based on a linear relationship between a value of the bite force coefficient for each tooth of the plurality of extracted unconservable teeth, and a value of the lost periodontal membrane area for each tooth;

finding an at-time-of-loss lost periodontal membrane area for each tooth of the plurality of extracted unconservable teeth based on the bite force-lost periodontal membrane straight line of the prepared chart;

calculating a periodontal index value at a time of loss of each tooth of the plurality of extracted unconservable teeth, based on an at-time-of-loss remaining periodontal membrane area determined by subtracting the at-time-of-loss lost periodontal membrane area from the total periodontal membrane area, wherein the periodontal index value at the time of loss=(at-time-of-loss remaining periodontal membrane area/total periodontal membrane area)×100(%);

creating a periodontal index chart for each tooth of the plurality of extracted unconservable teeth, the periodontal index chart comprising a line comprising a first segment extending between a first point having a value of 100 and a third point and a second segment connecting a second point having a value of 0 and the third point, wherein the first point represents a periodontal index value for the total periodontal membrane area, the second point represents a periodontal index value for a periodontal membrane area of 0, and the third point represents the periodontal index value at the time of loss of the respective tooth for the at-time-of-loss remaining periodontal membrane area;

calculating a remaining periodontal membrane area for one or more teeth in the patient's mouth, which are to be diagnosed for periodontitis;

predicting a periodontal index value for the one or more teeth in the patient's mouth to be diagnosed for periodontitis, the periodontal index value being based on the line of the periodontal index chart for one or more of the plurality of extracted unconservable teeth and the remaining periodontal membrane area for the one or more teeth in the patient's mouth to be diagnosed for periodontitis; and performing tooth extraction of the one or more teeth in the patient's mouth which are to be diagnosed for periodontitis as treatment for periodontitis for which the one or more teeth in the patient's mouth have an unknown remaining root surface area, when the predicted periodontal index value for the respective tooth is less than a predetermined value.

2. The method for diagnosing periodontitis and tooth extraction according to claim 1, wherein calculating the lost periodontal membrane area of each tooth comprises:

preparing a pseudo-root for the respective tooth from which the total periodontal membrane area of the respective tooth can be calculated quantitatively;

calculating the total periodontal membrane area of the respective tooth based on the pseudo-root; and calculating the lost periodontal membrane area of the respective tooth based on the total periodontal membrane area and the greatest sample attachment level.

3. The method for diagnosing periodontitis and tooth extraction according to claim 2, wherein the pseudo-root comprises a conical body in which a diameter (R) of a bottom of the conical body commensurate in shape with a root of the respective tooth is a diameter of the cementoenamel junction (CEJ) of each tooth, a height (H) of the conical body is a length of the root, and (M) is the greatest sample attachment level of the respective tooth, wherein the total periodontal membrane area (S) of the respective tooth based on the pseudo-root is calculated based on, $$S = \frac{\pi}{2} R \sqrt{\frac{R^2}{4} + H^2};$$

wherein the at-time-of-loss remaining periodontal membrane area $(S_S)$ is calculated from the pseudo-root based on $$S_s = \frac{\pi}{2}\left(R - \frac{RM}{\sqrt{\frac{R^2}{4} + H^2}}\right)\left(\sqrt{\frac{R^2}{4} + H^2} - M\right),$$

and wherein the lost periodontal membrane area $(S_L)$ is calculated from the pseudo-root by subtracting the at-time-of-loss remaining periodontal membrane area $(S_S)$ from the total periodontal membrane area (S) according to the equation $$S_L = \frac{\pi}{2}\left\{R\sqrt{\frac{R^2}{4} + H^2} - \left(R - \frac{RM}{\sqrt{\frac{R^2}{4} + H^2}}\right)\left(\sqrt{\frac{R^2}{4} + H^2} - M\right)\right\}.$$

4. The method for diagnosing periodontitis and tooth extraction according to claim 1, wherein the bite force coefficient is calculated based on $$B = \frac{TP}{AQ},$$

wherein T is the measured distance from the cusp of the respective tooth to the condyle of the temporomandibular joint; A is a distance from an incisal margin of a mandibular anterior first tooth to the condyle of the temporomandibular joint; P is a distance from an incisal vestibular surface angle of the mandibular anterior first tooth to a root apex; and Q is the expected distance between the cusp and the condyle for the respective tooth, which is defined as a distance from a site of occlusal contact to a farthest root apex of the respective tooth.

5. The method for diagnosing periodontitis and tooth extraction according to claim 1, wherein, when the at-time-of-loss remaining periodontal membrane area is set for a horizontal axis and the periodontal index value at the time of loss of the respective tooth is set for a vertical axis, creating the periodontal index chart for each tooth of the plurality of extracted unconservable teeth comprises:

drawing a straight line connecting the first point and the second point, plotting the third point, and drawing another straight line parallel to the straight line connecting the first point and the second point and passing through the third point; and preparing a periodontal index curve, which passes through the first point and the second point, and which contacts the straight line, which passes through the third point, only at the third point, and wherein predicting the periodontal index value for the one or more teeth in the patient's mouth to be diagnosed for periodontitis comprises identifying a point on the periodontal index curve corresponding to the remaining periodontal membrane area for the one or more teeth in the patient's mouth to be diagnosed for periodontitis.

* * * * *

UNITED STATES PATENT AND TRADEMARK OFFICE
CERTIFICATE OF CORRECTION

PATENT NO. : 10,285,635 B2
APPLICATION NO. : 14/389199
DATED : May 14, 2019
INVENTOR(S) : Yoshio Motegi Page 1 of 1

It is certified that error appears in the above-identified patent and that said Letters Patent is hereby corrected as shown below:

In the Claims

Column 26, Line 48, Claim 1, after "unconservable" insert -- , --

Signed and Sealed this
Thirtieth Day of July, 2019

Andrei Iancu
*Director of the United States Patent and Trademark Office*